(12) United States Patent
Valacich et al.

(10) Patent No.: US 10,524,713 B2
(45) Date of Patent: Jan. 7, 2020

(54) IDENTIFYING DECEPTIVE ANSWERS TO ONLINE QUESTIONS THROUGH HUMAN-COMPUTER INTERACTION DATA

(71) Applicant: Arizona Board of Regents for the University of Arizona, Tucson, AZ (US)

(72) Inventors: Joseph S. Valacich, Tucson, AZ (US); Jeffrey L. Jenkins, Provo, UT (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 191 days.

(21) Appl. No.: 14/899,865

(22) PCT Filed: Jun. 18, 2014

(86) PCT No.: PCT/US2014/043057
§ 371 (c)(1),
(2) Date: Dec. 18, 2015

(87) PCT Pub. No.: WO2014/205149
PCT Pub. Date: Dec. 24, 2014

(65) Prior Publication Data
US 2016/0143570 A1 May 26, 2016

Related U.S. Application Data

(60) Provisional application No. 61/837,153, filed on Jun. 19, 2013.

(51) Int. Cl.
*A61B 5/16* (2006.01)
*G06F 21/32* (2013.01)
(Continued)

(52) U.S. Cl.
CPC ............ *A61B 5/164* (2013.01); *G06F 21/316* (2013.01); *G06F 21/32* (2013.01); *G06F 21/40* (2013.01)

(58) Field of Classification Search
CPC ... A61B 5/0484; A61B 5/14553; A61B 5/164; G06F 11/3438; G06F 21/316;
(Continued)

(56) References Cited

U.S. PATENT DOCUMENTS 6,307,956 B1 * 10/2001 Black .................. G06F 3/03545
382/124
6,539,101 B1 * 3/2003 Black .................. G06F 3/03545
382/124
(Continued)

OTHER PUBLICATIONS

Lenz, Jorge M. The usage of handwritten dynamic (biometric) signatures in the digital world—and its implications. Nov. 14, 2007, FindBiometrics Global Identity Management website [retrieved Oct. 15, 2017] Retrieved online <URL: https://findbiometrics.com/the-usage-of-handwritten-dynamic-biometric-signatures-in-the-digital-world-and-its-impli.*

(Continued)

*Primary Examiner* — Eddy Saint-Vil
(74) *Attorney, Agent, or Firm* — Blank Rome LLP

(57) ABSTRACT

The present invention provides a system and a method for eliciting information to sensitive questions and reliably detecting whether one is being deceptive, concealing information, or experiencing a heightened emotional response to the question. In particular, the system and the method of the invention are based on analyzing the user behavioral biometric of using one or more input device(s).

18 Claims, 14 Drawing Sheets

(51) Int. Cl.
*G06F 21/62* (2013.01)
*G06Q 10/10* (2012.01)
*G06F 21/31* (2013.01)
*G06F 21/40* (2013.01)

(58) Field of Classification Search
CPC ........ G06F 21/32; G06F 21/36; G06F 21/554; G06F 21/577; G06F 21/40; G06Q 20/40; G06Q 20/4012
See application file for complete search history.

(56) References Cited

U.S. PATENT DOCUMENTS

| | | | |
|---|---|---|---|
| 6,871,287 B1 | 3/2005 | Ellingson | |
| 7,082,213 B2* | 7/2006 | Black | G06F 3/03545 382/115 |
| 7,961,917 B2* | 6/2011 | Black | G06F 3/03545 382/116 |
| 8,230,232 B2 | 7/2012 | Ahmed et al. | |
| 9,531,733 B2* | 12/2016 | Turgeman | H04L 63/126 |
| 9,536,071 B2* | 1/2017 | Turgeman | G06F 21/316 |
| 9,703,953 B2* | 7/2017 | Turgeman | G06F 21/554 |
| 2002/0054082 A1 | 5/2002 | Karpf | |
| 2005/0169504 A1* | 8/2005 | Black | G06F 3/03545 382/124 |
| 2006/0224898 A1 | 10/2006 | Ahmed | |
| 2007/0191691 A1 | 8/2007 | Polanco | |
| 2010/0293267 A1 | 11/2010 | Ribak et al. | |
| 2013/0091539 A1 | 4/2013 | Khurama et al. | |
| 2014/0078061 A1* | 3/2014 | Simons | G06F 3/03543 345/163 |
| 2016/0300054 A1* | 10/2016 | Turgeman | H04L 63/08 |
| 2016/0321445 A1* | 11/2016 | Turgeman | H04L 63/08 |
| 2016/0328572 A1* | 11/2016 | Valacich | A61B 5/7475 |

OTHER PUBLICATIONS

Chatterjee, Sutirtha; Sarker, Suprateek; Valacich, Joseph S. The Behavioral Roots of Information Systems Security: Exploring Key Factors Related to Unethical IT Use. Journal of Management Information Systems. Spring2015, vol. 31 Issue 4, p. 49-87. 39p.*
Jensen et al , Proceedings of the Rapid Screening Technologies, Deception and Credibility Assessment Symposium (Jan. 2013).

* cited by examiner

IDENTIFYING DECEPTIVE ANSWERS TO ONLINE QUESTIONS THROUGH HUMAN-COMPUTER INTERACTION DATA

CROSS-REFERENCE TO RELATED APPLICATIONS

This application claims the priority benefit of U.S. Provisional Application No. 61/837,153, filed Jun. 19, 2013, which is incorporated herein by reference in its entirety.

FIELD OF THE INVENTION

The present invention relates to a system and a method for eliciting information to sensitive questions that require use of an input device (e.g., keyboard and/or pointing device, etc.) and reliably detects whether one is being deceptive, concealing information, or experiencing a heightened emotional or cognitive response to the question by analyzing the input device usage characteristic. In particular, the system and the method of the invention are based on analyzing the user behavioral biometric of using one or more input device(s).

BACKGROUND OF THE INVENTION

The threat of malicious insiders is a top concern for government and corporate agencies. Insider threats—a trusted adversary who operates within an organization's boundaries—are a significant danger to both private and public sectors, and are often cited as the greatest threat to an organization. Insider threats include disgruntled employees or ex-employees, potential employees, contractors, business partners, and auditors. The damage caused by an insider threat can take many forms, including workplace violence; the introduction of malware into corporate networks; the theft of information, corporate secrets, or money; the corruption or deletion of data; and so on. According to a recent survey, it takes on average 416 days to contain an insider attack (HP Cyber Risk Report, 2012), and insider threats have been estimated to result in "tens, if not hundreds of billions of dollars" in damages. The identification process of insider threats is heightened in very large organizations. For instance, identifying a small number of potential insider threats within an organization with thousands of employees is a literal "needle in the haystack" problem.

Therefore, there is a need for a system and a method for determining whether a particular personnel poses an insider threat.

SUMMARY OF THE INVENTION

Some aspects of the invention address the insider threat challenge by providing a system and a method called ADMIT (i.e., Automated Detection Method for Insider Threat). In some embodiments, ADMIT is a web-based survey tool that elicits information to sensitive questions that requires an input device usage (e.g., keyboard, and/or a pointing device, etc.) and reliably detects whether one is being deceptive, concealing information, or experiencing a heightened emotional or cognitive response to the question by analyzing the input device usage characteristic.

Prior research on deception has established that humans guilty of acts known to be immoral, criminal, or unethical have uncontrolled physiological changes that can be detected as observable behavioral changes when responding to questions regarding such events. Similar to the way a polygraph (i.e., lie detector) detects physiological changes in the body based on uncontrolled responses when answering sensitive questions. The present inventors have discovered that such responses can be detected through monitoring a person's input device usage, (e.g., mouse and keystroke behavior) when a person is guilty of actions known to be wrong. Abnormal behavior that is indicative of insider threat can then be highlighted or alerted to specified individuals in the organization for review and further investigation. ADMIT operates like well-known web-based survey tools like SURVEYMONKEY® or QUALTRICS®, and thus can be mass deployed to an entire organization simultaneously.

In one embodiment, the system and the method are based on a subject's behavioral biometrics. The approach consists of establishing distinctive behavioral biometrics for a subject based on characteristic(s) of the subject's input device usage. The usage characteristic comprises how and the way the user uses the input device.

Some of the variables for how the user uses the input device include, but are not limited to, input device dynamics. For example, when the input device is a keyboard, the keyboard (i.e., input device) dynamics include, but are not limited to, the dwell time (the length of time a key is held down), transition time (the time to move from one key to another) and rollover time for keyboard actions. After these measurements are collected, the collected actions are translated and analyzed in order to determine the truthfulness of the subject's answer to a particular questionnaire. An algorithm can be used to generate a Keystroke Dynamics Signature (KDS), which is used as a reference profile for the subject using non-threatening or seemingly innocuous or harmless questions. In some embodiments, the KDS is constructed using a key oriented neural network based approach, where a neural network is trained for each keyboard key to best simulate its usage dynamics with reference to other keys.

When the input device is a pointing device such as a mouse, the pointing device dynamics include, but are not limited to, comparing selected pointing device actions generated by the subject as a result of subject's answer to an on-screen question or interaction with a graphical user interface (GUI) or any other display shown on the display screen. The data obtained from these actions are then processed in order to analyze the behavior of the user. Pointing device actions include general pointing device movement, drag and drop, point and click, and silence (i.e., no movement). The behavioral analysis utilizes neural networks and statistical approaches to generate a number of factors from the captured set of actions; these factors are used to construct what is called a Pointing Device Dynamics Signature (PDDS), a unique set of values characterizing the subject's behavior during both seeming innocuous or harmless questions and during a more direct question-and-answer sessions. Some of the factors consist of calculating the speed, total distance travelled, initial direction of movement, total response time, change in direction on the x-axis, change in direction on the y-axis, idle time, area under the curve, amount of deviation, reaction time, applied pressure, changes in angle, the pattern of a users' acceleration or deceleration during a movement, the precision of movements, the click latency, click pressure, or a combination of two or more thereof The detection algorithm for an input device calculates the significance of each factor with respect to the other factors, i.e. KDS, PDDS or other input device usage characteristics are weighted since certain actions are more prone to revealing truthfulness of the subject.

One particular aspect of the invention provides systems and methods for detecting deception in a subject. In one embodiment, this deception detection system (sometimes referred herein as ADMIT or "Automated Detection Method for Insider Threat") is a web-based survey tool that elicits information to sensitive questions and reliably detects whether one is being deceptive, concealing information, or experiencing a heightened emotional response to the question.

As discussed above, systems and methods of the invention can also include eliciting information from the subject on non-sensitive, benign, innocuous or seemingly harmless questions (i.e., control questions) to establish reference input device usage characteristics of the subject. Control questions can be presented at the beginning of the session or it can be interdispersed with sensitive questions to establish the reference input device usage characteristics of the subject. For example, the system and method can include randomly inserting or presenting to the subject control questions to determine the reference (or baseline) input device usage characteristic.

Alternatively, the reference input device usage characteristics can be based on the average input device usage characteristics of a plurality of subjects for a particular question. In this manner, the subject's input device usage characteristics (i.e., behavioral biometrics) can be compared to the "baseline" or the "reference input device usage characteristics" that consists of average or range of input device usage characteristic of a plurality of individual to the same question. Accordingly, the baseline or the reference input device usage characteristics can be based on the subject's own behavior biometrics during non-sensitive or non-threatening questionnaire session or it can be based on the input device usage characteristics of a plurality of subjects' input device usage characteristics for the same or similar question, or a combination of both.

In general, ADMIT is based on the discovery that humans guilty of acts known to be immoral, criminal, or unethical have uncontrolled physiological changes that can be detected as observable behavioral changes when responding to questions regarding such events. Similar to the way a polygraph (lie detector) detects physiological changes in the body based on uncontrolled responses when answering sensitive questions when a person is guilty of actions known to be wrong, the present inventors have discovered that such responses can be detected through use of an input device such as by monitoring mouse or other pointing device usage characteristics and/or keystroke usage characteristics. Abnormal behavior that is indicative of insider threat can then be highlighted or alerted to specific individuals in the organization for review and further investigation.

One particular aspect of the invention provides a behavioral biometric-based deception analysis system and/or method for determining whether a subject is truthful or deceptive to a question of interest (i.e., a sensitive question or key question). Such systems typically include displaying the question (e.g., on a computer screen or projecting the question on a display). The subject is then allowed to select or input subject's answer to the question presented using one or more input device. The system includes a data interception unit that is configured to intercept input from the subject who is directed to a question presented on a display screen. The data interception unit is configured to passively collect an input device (e.g., a pointing device, such as a mouse, a touch screen, a touch pad, a stylus, a track ball, etc.) usage characteristic. The system also includes a behavior analysis unit operatively connected to said data interception unit to receive the passively collected input device usage characteristic; and a behavior comparison unit operatively connected to said behavior analysis unit. In some embodiments, the system dynamically monitors and passively collects behavioral biometric information (i.e., input device usage characteristics), and translates the behavioral biometric information into representative data, stores and compares results, and outputs a result associated with truthfulness or deception to the question of interest presented on the display screen.

In some embodiments, said behavior comparison unit is operatively connected to an application or program that presents a question on the display screen such that said behavior comparison unit influences the next question presented on the display screen by the application using a decision tree structure based on the result. Thus, for example, if the subject's behavior biometrics is ambiguous or inconclusive, a follow-up type of question can be displayed to further analyze the subject's behavior biometrics to a particular sensitive question.

Yet in other embodiments, the input device usage characteristics comprise pointing (e.g., mouse, joystick, stylus, trackball, etc.) device usage characteristics. In some instances, the pointing device usage characteristics comprise movement of said pointing device between the starting position of said pointing device and the answer selected by the subject on the display screen, the elapsed time between presentation of the question on the display screen and the a selection of the answer by the subject, the speed, total distance travelled, initial direction of movement, total response time, change in direction on the x-axis, change in direction on the y-axis, idle time, area under the curve, amount of deviation, reaction time, applied pressure, changes in angle, acceleration, the precision of movements, the click latency, click pressure, or a combination of two or more thereof.

When the pointing device is a touch screen or a touch pad, the usage characteristic can include finger movement, precise timing, and applied pressure between the initial position of a pointer and the answer on the display screen selected by the subject. In addition or alternatively, the input device usage characteristic can include characteristic can include speed, total distance travelled, initial direction of movement, total response time, change in direction on the x-axis, change in direction on the y-axis, idle time, area under the curve, amount of deviation, reaction time, applied pressure, changes in angle, the pattern of a users' acceleration or deceleration during a movement, the precision of movements, the click latency, click pressure, or a combination of two or more thereof. The term "area under the curve" refers to the area formed by the total distance or actual direction travelled by the user starting from the starting position of the pointer $(x_1, y_1)$ to the answer selected by the subject $(x_2, y_2)$, and the distance between $y_1$ and $y_2$ (i.e., absolute value of $y_1$-$y_2$) and the distance between $x_1$ and $x_2$. (i.e., absolute value of $x_1$-$x_2$).

Still in other embodiments, said input device (e.g., pointing device such as mouse) usage characteristic is based on the speed, total distance travelled, initial direction of movement, total response time, change in direction on the x-axis, change in direction on the y-axis, idle time, area under the curve, amount of deviation, reaction time, applied pressure, changes in angle, the pattern of a users' acceleration or deceleration during a movement, the precision of movements, the click latency, click pressure, or a combination of two or more thereof Yet in other embodiments, the behavior comparison unit compares the result of the subject's behavioral biometric to a reference behavioral biometric. In some instances, the reference behavioral biometric comprises the subject's behavioral biometric to a non-interested or non-sensitive question. In other embodiments, the reference behavioral biometric comprises behavioral biometric of a plurality of subjects based on the same non-interested or non-sensitive question. Still alternatively, the reference behavioral biometric can comprise behavioral biometric of a plurality of subjects who answered truthfully on the same sensitive question or who answered non-truthfully on the same sensitive question. It should be noted in this case, the reference behavioral biometric can comprise an average of behavioral biometric obtained from the plurality of subjects. Alternative, the reference behavioral biometric can be based on a desired confidence limit (e.g., 95%) under the standard curve. In this latter reference behavioral biometric, the subject's behavioral biometric is analyzed to determine whether it is within the desired confidence limit range.

In one particular embodiment, said reference behavioral biometric comprises an average behavioral biometric to the same question presented on the display screen of a plurality of subjects.

Yet in other embodiments, said behavioral biometric-based deception analysis system is suitably configured for real-time deception analysis.

Still in other embodiments, said data interception unit is further configured to passively collect keyboard usage characteristic of the subject. In some instances, said keyboard usage characteristic comprises what key was pressed, what time (e.g., elapsed time between presenting the question on the display screen and the time) a key was pressed, what time it was released, or a combination thereof. Moreover, said keyboard usage characteristic can be based on or includes at least one of speed, transition time, dwell time, pressure of key pressed, or a combination thereof.

Yet another aspect of the invention provides a method for determining whether a subject is truthful or deceptive to a question of interest, said method comprising:
(a) presenting a question of interest and a plurality of answers on a display screen that requires use of an input device;
(b) allowing a subject to select an answer using the input device (e.g., a pointing device, a keypad, a touch pad, or a touch screen);
(c) passively collecting subject's input device usage characteristic;
(d) comparing subject's input device characteristic with a reference input device usage characteristic to determine whether the subject is truthful or deceptive to the question of interest; and
(e) optionally repeating steps (a)-(d) with a different question.

The different question can be a non-sensitive question to further establish the subject's reference behavior biometrics. It can also be another sensitive question or a follow-up question to further establish the truthfulness of the subject.

In some embodiments, such a method can further comprise the steps of:
(a) presenting a benign or control question and a plurality of answers on a display screen that requires use of the input device;
(b) allowing the subject to select an answer using the input device;
(c) passively collecting input device usage characteristic of the subject;
(d) storing passively collected input device usage characteristic of the subject as the reference input device usage characteristic (i.e., reference behavior biometrics); and
(e) optionally repeating steps (a)-(d) with a different question.

Still in other embodiments, said reference input device usage characteristic is an average input device usage characteristic of a plurality of subjects for the same question of interest. It should be noted that such reference input device usage characteristics can be either of those subjects who have truthfully answered the question or input device usage characteristics of those subjects who did not truthfully answer the question. Alternatively, the method can compare to both of these subjects to determine which reference input device usage characteristics more closely resembles the subject's input device usage characteristics.

Yet in other embodiments, said input device usage characteristic comprises input device movement between the starting position of input device and the answer selected by the subject on the display screen.

In other embodiments, said input device usage characteristic is based on at least one of speed, total distance travelled, initial direction of movement, total response time, change in direction on the x-axis, change in direction on the y-axis, acceleration, idle time, area under the curve, amount of deviation, reaction time, applied pressure, and changes in angle.

DETAILED DESCRIPTION OF THE INVENTION

Figure 1:
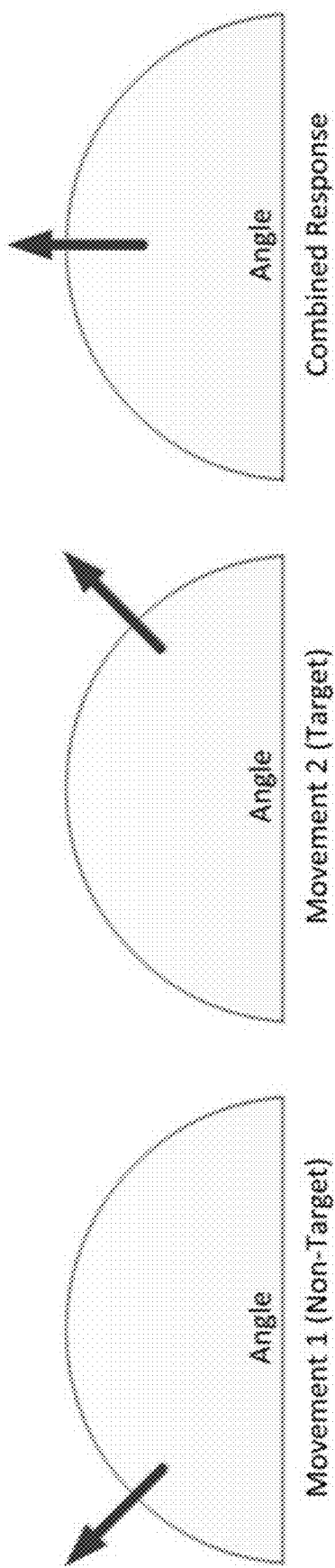
FIG. 1 is a schematic representation showing combined mouse movement resulting when multiple answers catch a respondent's attention.

The present inventors have discovered that input device (e.g., mouse and/or keyboard, other input devices known to one skilled in the art, an other input devices that are developed) usage features or characteristics are diagnostic of insider threats in sensitive questions (i.e., questions about insider threat activities or other key or security questions) administered on a computer. Some aspects of the invention are based on the discovery by the present inventors that when people see two or more answers to a question that catch or draw their attention (e.g., a truthful answer and a deceptive answer that the person will ultimately choose), the mind automatically starts to program motor movements toward both answers simultaneously. To eliminate one of the motor movements (e.g., eliminate the movement towards confessing to an insider threat activity), the mind begins an inhibition process so that the target movement can emerge. Inhibition is not immediate, however, but rather occurs over a short period of time depending on the degree both answers catch the respondents attention (up to ~750 milliseconds or more). If movement begins before inhibition is complete, the movement trajectory is a product of motor programming to both answers. See FIG. 1. Thus, in an ADMIT survey, when people are asked a question about an insider threat activity and the incriminating answer catches their attention, their mouse trajectory is biased toward this incriminating answer (measured on an x, y axis) on its way toward the non-incriminating (e.g., deceptive) answer. For innocent people, the incriminating answer generally does not catch their attention to the same degree, and thus inhibition occurs more quickly and their mouse movements is less biased toward the opposite response.

In addition, being deceptive normally causes an increase in arousal and stress. Such arousal and stress causes neuromotor noise that interferes with people's fine motor skills (e.g., using the hand and fingers to move a mouse or use a touch screen to answer a question). As a result, the precision of mouse movements decreases when people are being deceptive, ceteris paribus. To reach the intended target (e.g., a deceptive answer in the ADMIT survey), people automatically and subconsciously compensate for this decrease in precision through reducing speed and creating more adjustments to their movement trajectories based on continuous perceptual input. Thus, in ADMIT surveys, the present inventors have found that people exhibit slower velocity, more adjustments (x and y flips), greater distance, and more hesitancy when being deceptive compared to when telling the truth.

As another example, the present inventors have found that people guilty of insider threat activities display different mouse movements on non-incriminating questions compare to innocent people. In anticipation of a question that might incriminate them, guilty people show a task-induced search bias: before answering a question, they take a fraction of a second longer to evaluate the question. After seeing that the question is not relevant, they then move more quickly to the truthful answer than innocent respondents. Table 1 summarizes examples of mousing features that can be used to differentiate between how guilty insiders and innocent respondents respond to ADMIT questions. In some embodiments at least four or more, typically at least eight or more, often at least ten or more, still more often at least fifteen or more, and most often at least twenty or more of these characteristics are determined and analyzed. Still in other embodiments, all of the input device usage characteristics in Table 1 are determined and analyzed.

TABLE 1

Examples of features that distinguish an insider threat (exemplary features monitored)

| Statistic | Description |
| --- | --- |
| X | The X coordinates for each movement |
| Y | The Y coordinates for each movement |
| Z | The Z coordinate for each movement |
| Pressure | The pressure for each movement |
| Rescaled X | The X coordinates for the interaction normalized for screen resolution |
| Rescaled Y | The Y coordinates for the interaction normalized for screen resolution |
| X Average | The X coordinates averaged in buckets of 75 ms |
| Y Average | The Y coordinates averaged in buckets of 75 ms |
| X Norm | The X coordinates time normalized |
| Y Norm | The Y coordinates time normalized |
| Pressure | The pressure applied to the mouse for every raw recording |
| Timestamps | The timestamp for every raw recording |
| Click Direction | Whether the mouse button was pushed down (d) or released (u) for every time an action occurred with the mouse button |
| Click X | The X coordinates for each mouse click event |
| Click Y | The Y coordinates for each mouse click event |
| Click Rescaled X | The X coordinates for each mouse click event normalized for screen resolution |
| Click Rescaled Y | The Y coordinates for each mouse click event normalized for screen resolution |
| Click Pressure | The pressure applied to the mouse for every raw recording |
| Click timestamps | The timestamp for every mouse click event |
| Acceleration | The average acceleration for each 75 ms |
| Angle | The average angle for each 75 ms |
| Area Under the Curve (AUC) | The geometric area between the actual mouse trajectory and the idealized response trajectory (i.e., straight lines between users' mouse clicks); it is a measure of total deviation from the idealized trajectory. |
| Additional AUC | The AUC minimum the minimum AUC |
| Overall Distance | The total distance traveled by the mouse trajectory |
| Additional Distance | The distance a users' mouse cursor traveled on the screen minus the distance that it would have required to traveling along the idealized response trajectory (i.e. straight lines between users' mouse clicks), |
| Distance Buckets | Distance traveled for each 75 ms |
| X Flips | The number of reversals on the x axis |

TABLE 1-continued

Examples of features that distinguish an insider threat (exemplary features monitored)

| Statistic | Description |
| --- | --- |
| Y Flips | The number of reversals on the y axis |
| Maximum Deviation | The largest perpendicular deviation between the actual trajectory and its idealized response trajectory (i.e., straight lines between users' mouse clicks), |
| Speed Buckets | Average speed for each 75 ms |
| Overall Speed | Average overall speed |
| Idle Time | if there is a change in time greater than 200 ms but no movement, this is counted as idle time |
| Idle Time on Same Location | If there is a change in time but not a change in location, this mean an event other than movement triggered a recording (e.g., such as leaving the page, and other things). The time in this event is summed. |
| Idle Time On 100 Distance | If there is a change in distance greater than 100 between two points, this may indicate that someone left the screen and came back in another area |
| Total Time | Total response time |
| Click Mean Speed | The mean speed of users click |
| Click Median Speed | The median speed of users click |
| Click Mean Latency | The mean time between when a user clicks down and releases the click |
| Click Median Latency | The median time between when a user clicks down and releases the click |
| Answer Changes | The number of times an answer was selected; if over 1, the person changed answers |
| Hover Changes | The number of times an answer was hovered; if over 1, the person hovered over answers they didn't chose |
| Hover Region | The amount of time a person overs over a region |
| Return Sum | The number of times a person returns to a region after leaving it |
| Dwell | The measurement of how long a key is held down |
| Transition | Time between key presses |
| Rollover | The time between when one key is released and the subsequent key is pushed |

Figure 2:
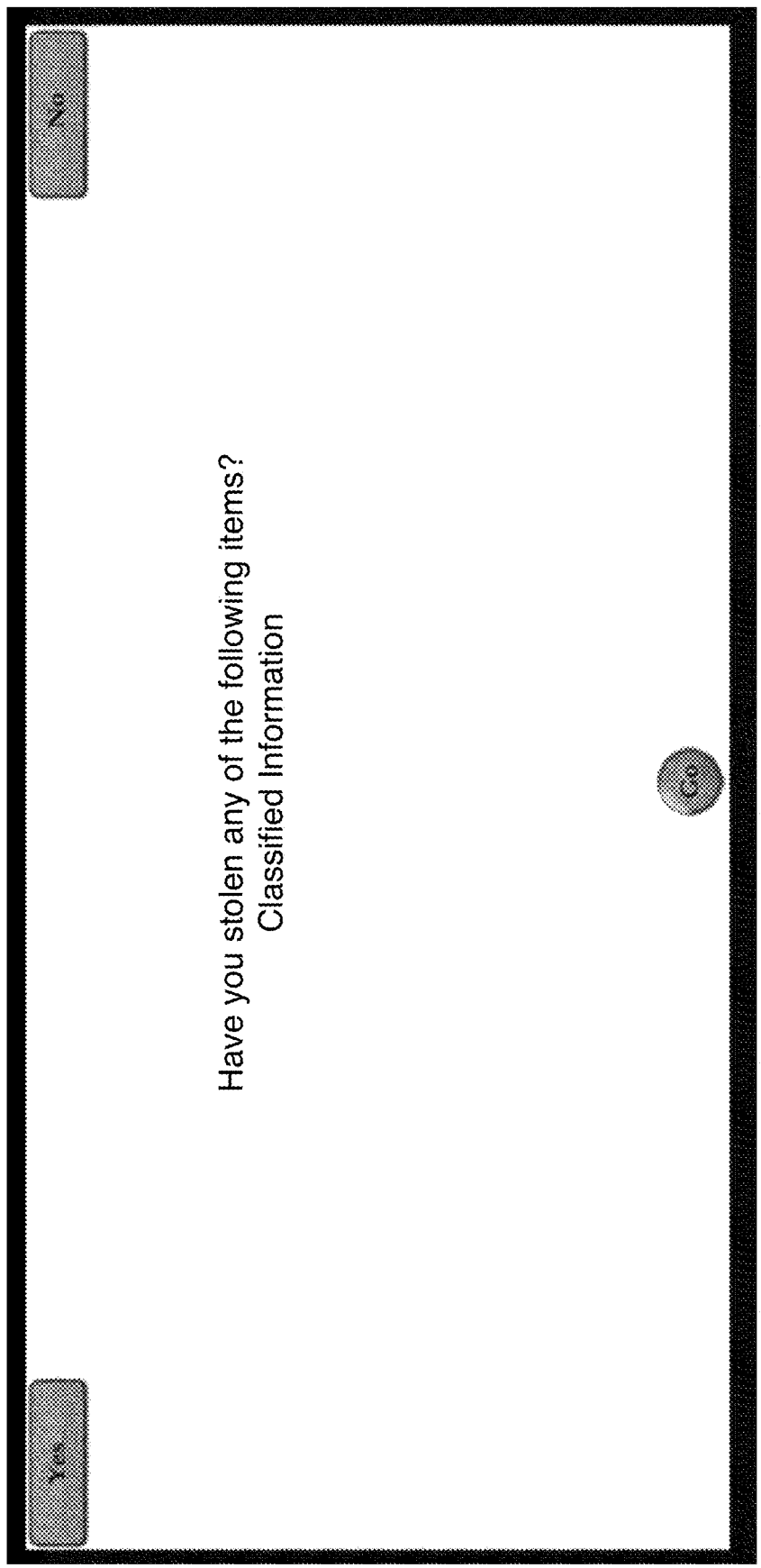
FIG. 2 is an example of insider threat question.

System Implementation:

ADMIT asks specially designed questions on a computer about illicit behavior and requires respondents to answer by admitting to or denying the behavior by dragging a button on the bottom of the screen to 'yes' or 'no'. Following polygraph techniques (the concealed information test, control question test, comparative questions test, etc.) survey items are normally crafted to conform to at least two categories: benign questions that can be used to establish baseline behavioral data, and sensitive questions that the organization is interested in the answer to. Responses are analyzed with both with-in subject comparisons as well as by comparing responses with the aggregate responses of other employees. For instance, FIG. 2 is an example of an insider threat question—"have you stolen any classified information?" In this example, the respondent must move the mouse from the lower middle of the screen to the "No" answer to deny stealing classified information or to "Yes" to confess. Mouse movements are captured while the respondent is answering the question and compared to an individual baseline (how the individual moves the mouse on truthful responses) and/or to a population baseline (how other people normally move the mouse on this question) to detect deception.

Figure 3:
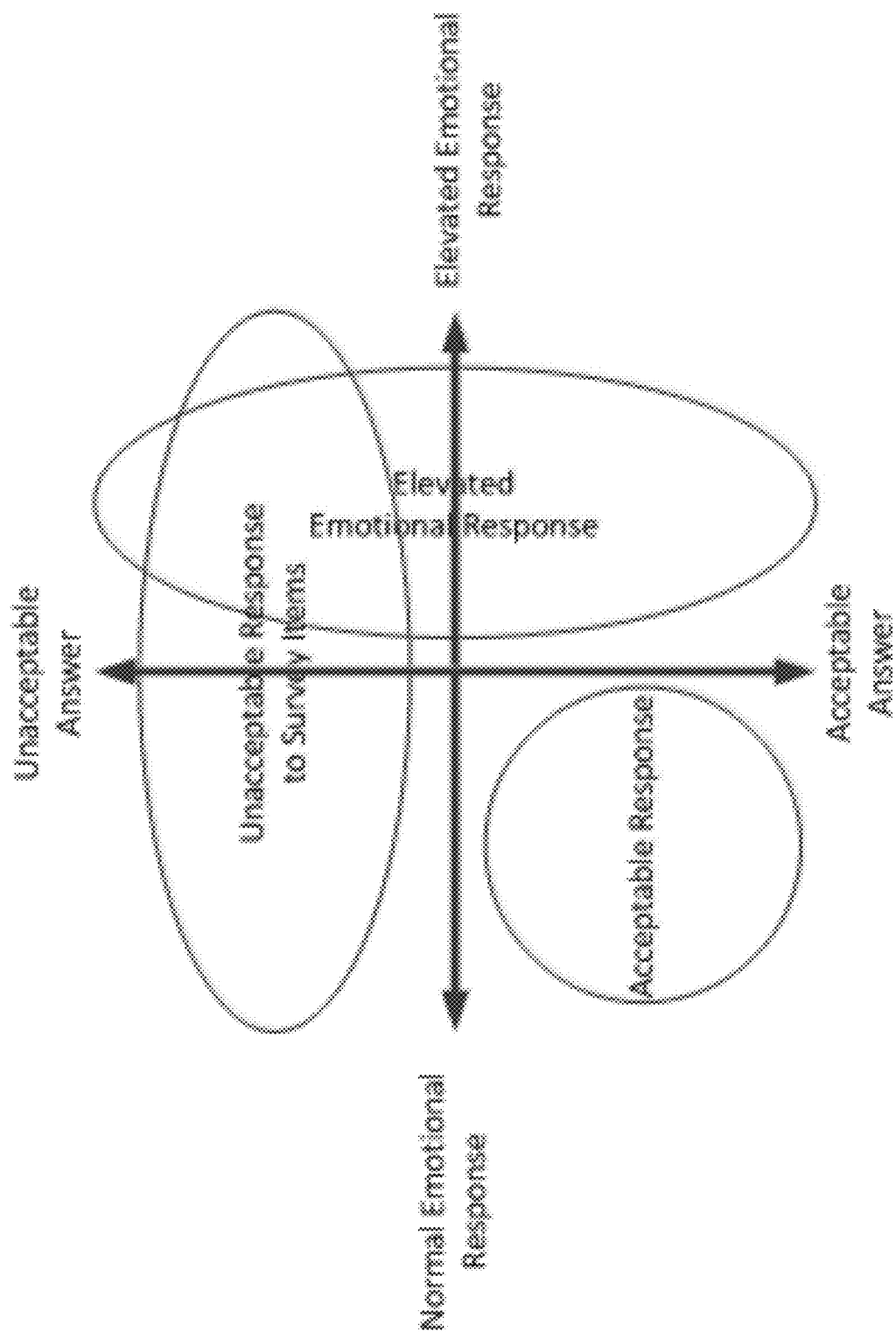
FIG. 3 is an example of one particular embodiment of ADMIT response analysis framework.

Survey items (e.g., questions) have acceptable and non-acceptable ranges of responses. See FIG. 3. These acceptable response ranges will be determined by the individual organization involved in the survey. For example, if the question were asked "A crime was committed in our organization. If you committed the crime, you will know what act was performed. Did you perform any of the following crimes?" The system would then list 6 options (e.g., unauthorized disclosure of classified information, theft of credit card numbers, theft of hardware, etc.). For the key item (the item of interest), a threshold is set on abnormal mouse movements; any abnormal mouse movements above this threshold is deemed as unacceptable (and anything below, acceptable). By observing both the answer provided by the user and using the mouse and keyboard behavior to detect changes in emotional response, one can make four potential observations about a response to a survey item using ADMIT (FIG. 3): (i) Lower Left Quadrant: Answer was within acceptable range with normal emotional response (i.e., no action is necessary); (ii) Upper Left Quadrant: Answer is outside acceptable range with normal emotional response (i.e., an HR problem and alert needs to be generated); (iii) Upper Right Quadrant: Answer is outside acceptable range with elevated emotional response (i.e., an HR problem and alert needs to be generated); and (iv) Lower Right Quadrant: Answer was within acceptable range, however, with an elevated emotional response (i.e., a deceptive answer; an investigation needs to be launched).

Several functionalities can be implemented in the ADMIT system to facilitate accurate and reliable analysis of mouse movements. For example, (i) Data is time-normalized (e.g., all trajectories are evenly split into 101 equal buckets) to compare trajectories between respondents for detecting deception; (ii) Data is averaged into 75 ms duration intervals to account for differences in computers speeds and mouse characteristics within subjects; (iii) Data is rescaled to a standard scale to account for the trajectories of respondents who used different screen resolutions; (iv) Respondents are required to start moving their mouse or finger before an answer is shown, so that a respondent's initial movements can be captured as soon as they see the answer; (v) If respondents stop moving their mouse or finger or stop dragging an answer, an error is shown; (vi) To help respondents get use to the testing format and improve the performance of the evaluation, a tutorial and practice test can be provided; (vii) All items (sensitive and control items) can be pilot tested to make sure innocent people respond as intended; (viii) A tree-like questioning framework can be implemented to ask follow-up questions when deception is detected or suspected; (ix) All input device usage characteristics (such as mousing data) can be sent to a server data server via a web service to be analyzed for deception. This reduces the likelihood that data can be tampered with during the analysis; (x) A secure management dashboard can be implemented to visualize (e.g., in real-time) the results and execute policy-driven responses to threats; (xi) Probabilities of deception can be calculated based on multi-tiered testing; and/or (xii) Different features of deception are extracted for different devices (desktop, iPad, etc.).

ADMIT system introduces a lightweight and easily deployable system for quickly identifying potential threats. Many agencies go to significant lengths, and at great expense, to identify potential threats. Unfortunately, current techniques used to identify potential threats are labor intensive, laden with bias, and frequently miss potential threats. For instance, polygraphs are often used for employee initial and ongoing screening, but are extremely problematic for widespread deployment. A single polygraph test requires hours of pre-planning, pre-test interviewing, testing, and post-testing reviews, costing hours of productive time and thousands of dollars per administration. Other methods such as conducting face-to-face interviews (that must be done individually and at great expense) or traditional surveys (which are cheap to deploy but easy to subvert) are equally constrained. ADMIT can be deployed simultaneously to thousands of employees at minimal expense. Additionally, by eliminating humans and creating an objective methodology for identifying possible insider threats, ADMIT is not subject to the same biases that more conventional methods may fall victim to. Thus, ADMIT improves upon previous methods in at minimum the following ways: (i) Easy and inexpensive to deploy to a large number of employees simultaneously; (ii) A data capture process runs in the background during survey administration, while analysis can take place on a separate and secure remote system; (iii) Behavioral sensing data (e.g., keyboard and mouse usage) is gathered in an unobtrusive manner with no adverse effect to the user; (iv) Users need not be aware of the data collection that is taking place; (v) Unlike systems that rely on linguistic features, the system's behavioral analysis approach is language agnostic (i.e., the detection methodology will work with English, Spanish, Arabic, etc.) because it relies on system usage patterns rather than message content; (vi) Survey items or questions are specifically constructed to identify behaviors of interest; i.e., ADMIT can be deployed in a broad range of contexts, e.g., employment applications, healthcare (doctor or insurance), life insurance, loan application, ongoing employment screening, financial disclosure, etc.; (vii) The system is not easily fooled, as heightened emotions that would trigger anomalous event typically manifests itself as subtle differences in typing or mouse movement behavior that occurs between 20 and 100 milliseconds. Attempts to modify one's keystroke or mouse use can be flagged as abnormal, thus identifying individuals attempting to fool the system; and (viii) The system is not subject to biases that are common in face-to-face investigations.

ADMIT can be used to confirm the individuals that are operating within a given acceptable range of behavior and system usage. It also provides a powerful tool for management to proactively identify and investigate those individuals who respond abnormally to targeted questions. ADMIT provides unprecedented and innovative capabilities to identify those individuals that are potentially a threat to the effective operation of an organization.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Below is an example study conducted to validate ADMIT. This is only an example. In other types of assessments, the same or different factors may or may not be significant.

A mock theft study was conducted using a multi-level experiment design (2). Half of the participants were randomly assigned to commit an insider threat activity (steal sensitive information). All participants—both innocent and guilty—then completed a computer-based screening test (an ADMIT test) that asked questions about the insider threat activity (i.e., key questions) and benign questions not related to the activity (i.e., control questions).

TABLE 2

Multi-level experiment design

| Level 1 | Committed the insider threat activity | | Did not commit the insider threat activity | |
|---|---|---|---|---|
| Level 2 | Key questions | Control questions | Key questions | Control questions |

Participants:

A total of 75 people were recruited for the experiment from an undergraduate business course for extra credit. Of these, 5 of the participants in the guilty treatment refused to perform the mock insider threat theft. Four others confessed to committing the theft during the screening. This resulted in useable data from 66 participants (30 in the insider threat treatment and 36 in the innocent treatment). 59% of participants were female and the average age was 21.8. The average number of years of college education was 3.1. The most represented nationalities were American (69%), Chinese (11%), and Mexican (9%). Twenty-nine percent of students were business management majors, 27% accounting, 20% marketing, 15% finance, and 9% management information systems.

Procedures:

A task was designed to mimic a realistic insider threat scenario. Although the task was sanctioned (i.e., participants were told to perform the elicit act and appear innocent), it was conducted to solicit suspicion and anxiety. Participants registered for an appointment online and were randomly assigned to an innocent or guilty condition. Upon arriving at the experiment, the participant was given a consent form to review and sign.

Guilty Condition:

Participants in the guilty condition were given a folded piece of paper and a jump drive. They were instructed to go in the elevator (on the first floor), press the button to the fourth floor, and only then read the paper. The instructions on the paper are shown in Table 3. In summary, the instructions asked participants to go to the Management Information Systems department, login to a computer in the front office using a set of credentials, and steal a file containing department credit card numbers. Participants were instructed to lie if confronted about the theft.

TABLE 3

Guilty participant instructions

Your task is to commit a theft. You will go into the MIS department front office and steal a computer file that contains department credit card numbers. You will then go to room 109 for further instructions. During the entire experiment, please try your best to appear innocent, do not raise any suspicion, and do not confess to committing the theft. If you are asked any questions about the theft, LIE.
Below are the steps of your task:
 1. Go to the MIS Department front office-room 430 (see the first picture).
 2. Go to the back-right corner of the reception area (circled in the lower picture; under the TV). Be confident. Don't talk with anyone unless talked to. If anyone asks what you are doing, say you are a TA, and you need to get a file.
 3. Log in to the computer on the desk. Use the following credentials:
 4. Username: CHROME13\eller
 5. Password: manager
 6. You should see a picture of a red sports car as the desktop background and a file called "department credit card numbers"
 7. Open the file to make sure it contains the department credit card numbers
 8. Copy the entire file to the given flash drive. You can plug the flash drive into the monitor or on the computer to the left side of the desk. DO NOT REMOVE THE FILE, JUST COPY IT.
 9. Log out of the computer.
 10. Go to room 109 with the flash drive when you are finished.
To make sure you remember the details of this theft, please answer the following questions:
What picture was on the desktop of the computer? _____
What information was in the file you stole? _____
Where did you copy the file to? _____
What password did you use to login to the computer? _____

Guilty participants then were instructed to go back to the room on the first floor. Upon arriving at the room, an experiment facilitator explained that a theft occurred and the participant was a suspect for that theft. The participant was then asked to take an investigation screening (an ADMIT test).

Innocent Participants:

Participants in the innocent condition were also given a folded piece of paper. They were instructed to go in the elevator (on the first floor), press the button to the fourth floor, and then read the paper. Similar to the guilty participants, the paper asked participants to go to the Management Information Systems department. However, rather than stealing information, innocent participants were asked to pick up a piece of paper (a news article) at the front desk and then go back to the room on the first floor. Upon arriving at the room, an experiment facilitator explained that a theft occurred and the participant was a suspect for that theft. The participant was then asked to take an investigation screening (ADMIT test described below).

ADMIT Test:

The ADMIT test consisted of a concealed information test (CIT) adapted to the ADMIT format and then several follow-up questions. All questioning was presented on a computer. The CIT is the most scientifically validated polygraph questioning technique (Ben-Shakhar and Elaad 2003; Council 2003; Fiedler et al. 2002). The objective of the CIT is to detect if a person has 'inside' or 'concealed' knowledge of an activity (e.g., stealing the credit card numbers) (Ben-Shakhar and Elaad 2003). In a standard CIT, the person being interviewed is presented a question or a stimulus about a specific target (e.g., a crime). In a face-to-face CIT, the interviewer verbally asks the interviewee a question such as, "Very important information was stolen today from a computer. If you committed the theft, you will know what was stolen. Did you steal any of the following information today?" The interview then recites five to six plausible answers. For example, the interviewer might recite: 'passwords', 'credit card numbers', 'exam key, 'social security numbers', 'health records', or 'encryption codes'. Usually, the interviewee is asked to verbally repeat the possible answer and then respond 'yes' or 'no'. One of the plausible answers should relate directly to the target under investigation. This is referred to as the key item. For example, if the CIT is investigating theft of 'credit card numbers', this answer must be included in the set of answers accompanied by several other plausible yet unrelated answers (Krapohl et al. 2009). An innocent person with no insider knowledge' should exhibit the same amount of arousal for each answer. However, a guilty person should experience a detectable psychophysiological change—an orienting response—when presented the key item.

In designing the CIT for ADMIT in this experiment, all of the items (key and control items) were pilot tested to make sure that an innocent person will respond similarly to each item without unintended psychophysiological responses. Next, prior to administering the CIT, each participant was familiarized with the format of the CIT through a practice test. In the practice test, the program required the respondent to move the mouse within the first second, or displayed an error. This helps ensure the inhibition is not complete before movement occurs. This also reduces the likelihood that an orienting response would occur due to the novel format of the test and therefore confound the results (Krapohl et al. 2009). CIT was then administered to investigate the theft of the credit card numbers. The CIT was administered by a computer, rather than by a human facilitator. Screenshots and explanations of the CIT are shown in Table 4.

In designing the CIT for ADMIT in this experiment, all of the items (key and control items) were pilot tested to make sure that an innocent person will respond similarly to each item without unintended psychophysiological responses. Next, prior to administering the CIT, each participant was familiarized with the format of the CIT through a practice test. In the practice test, the program required the respondent to move the mouse within the first second, or displayed an error. This helps ensure the inhibition is not complete before movement occurs. This also reduces the likelihood that an orienting response would occur due to the novel format of the test and therefore confound the results (Krapohl et al. 2009). CIT was then administered to investigate the theft of the credit card numbers. The CIT was administered by a computer, rather than by a human facilitator. Screenshots and explanations of the CIT are shown in Table 4.

TABLE 4

Experiment ADMIT test

| Screen display | Explanation |
|---|---|
| Very important information was stolen today from a computer. If you committed the theft, you will know what was stolen. Did you steal any of the following information today? (Press enter to see the possible answers) | The question for the first question is presented to the user |
| YES NO Next | After pushing Enter, the user must move the mouse to the bottom-middle of the screen to push next before seeing the first item. This anchors the mouse in the same location for each item. |
| YES NO Did you steal any of the following Information today? Passwords Next | The first item (passwords) is shown. The user must move the mouse from the bottom middle of the screen to the upper right or left hand corners to answer the question. The first item is always thrown out because its novelty may solicit an orienting response (Krapohl et al. 2009). Thus, the first item is not randomized. The program requires the respondent to move the mouse within the first second, or display an error (the respondent becomes accustom to this in the practice test preceding the question). |
| YES NO Next | Second item - last item: The mouse is anchored at the bottom of the screen prior to displaying the next item. |
| YES NO Did you steal any of the following Information today? Credit card numbers Next | Second item - last item: Display the remaining items in random order, including the key item. The items in random order included: Credit Card Numbers Exam Key Social Security Numbers Health Records Encryption Codes The program requires the respondent to move the mouse within the first second, or display an error (the user becomes accustom to this in the practice test preceding the question). |

Measures:

Mouse and electrodermal data were collected from each subject. The electrodermal response data is typically used in CIT polygraph testing. It was used here to compare to and validate the procedure for detecting insider threats based on mouse movements.

Mousing:

ADMIT performs several transformations and computations to facilitate analysis as follows: (i) Space rescaling—All mouse trajectory data were rescaled to a standard coordinate space (a 2×1.5 rectangle that is compatible with the aspect ratio of the computer screen). The top left corner of the screen corresponds to -1, 1.5, and the bottom right corner of the screen corresponds to 1,0. Thus the starting position is at position 0, 0; (ii) Remapping—All data were remapped so the mouse started at position 0,0. Although the user must click a button at the middle-bottom of the screen to see the next item, the button's size allows variations to exist (e.g., someone might actually click on the right side of the button). Thus, the trajectories are remapped for comparison; (iii) Time normalization—Time normalization was required for analysis of spatial attraction/curvature and complexity such as maximum deviation (maximum perpendicular deviation between the straight line trajectory), area under the curve (geometric area difference between the actual trajectory and the straight line), and x-flips and y-flips. The rational for time normalization is that recorded trajectories tend to have different lengths. For example, a trial that lasts 800 ms will contain 56 x, y coordinate pairs. However, a trial that last 1600 ms will contain 112 x,y coordinate pairs. Using linear interpolation, trials with different numbers of x, y coordinate pairs is divided up into 101 time-steps for average and comparison across multiple trials and computation of the aforementioned features; and (iv) Raw time analysis—For other analyses (velocity, acceleration, angle), the x, y location were analyzed for raw time (not normalized time) for the first 1500 ms. The x, y locations were averaged in intervals of 75 ms to account for the computers limitations of capturing movements at about 70 hz. Only the first 1500 ms were analyzed because most people take at least 1500 ms to respond.

Electrodermal Responses:

Using a polygraph machine, electrodermal responses were also captured using two sensors on the pointer and ring fingers of the participant's non-dominant hand (the hand not used to move the mouse). 12 seconds were allowed between each question/item for an individual's electrodermal activity to react and then to level out before asking the next question (Gamer et al. 2006).

Pilot Tests:

This test builds on 7 exploratory pilot studies with approximately 1293 participants to understand the dynamics of capturing mouse movements to detect deception, to validate that the items do not inherently cause an unanticipated response for an innocent person, and to discover what features to extract and analyze to detect deception and facilitate hypothesis creation. The specific scenario used in this experiment, was pilot tested with an additional 6 people to make final adjustments to the experiment protocol and tests.

Analysis:

Analysis were divided into three relevant areas to detect insider threats: (i) Area 1 examined what features differentiated how a guilty person answers a key question versus a control question (a within-subject analysis). This is a typical analysis done in polygraph administration; (ii) Area 2 examined what features differentiated between how a guilty person answers a key question versus how an innocent person answers a key question (a between-subject analysis); and (iii) Area 3 examined what features differentiated between how a guilty person answers a control question versus how an innocent person answers a control question (a between subject-analysis).

Other possible areas of analysis were excluded at least in part for the following reasons: (i) Confessing to an act, whether truthfully or deceptively, will always flag the response for follow-up questioning. Hence, this eliminates the need to create a model to predict: a) when guilty people are being deceptive on a control question (falsely confessing), b) when deceptive people are being truthful on a key question (confessing), and c) when innocent people are being deceptive on either a key question or control question (falsely confessing); and (ii) Important for the validity of the CIT, innocent people should experience no systematic difference in how they response to key and control questions. This was confirmed through pilot testing. Hence, a model differentiating between the two types of questions for innocent people was not needed.

Table 5 summarizes the areas of analysis. The analysis proceeded as follows. For each area, determination was made to see if there was a difference in electrodermal response as done in traditional polygraph testing. Determination was also made to see if differences in mousing behavior also existed.

TABLE 5

Summary of areas of analysis

| Area 1: Guilty key vs. control questions | | Area 2: Key questions | | Control Questions | |
|---|---|---|---|---|---|
| Guilty control questions (truthful response) | Guilty key questions (deceptive response) | Innocent key questions (truthful response) | Guilty key questions (deceptive response) | Innocent control questions (truthful response) | Guilty control questions (truthful response) |

Guilty Key Vs. Control Items:

First, whether differences can be detected was investigated in how guilty individuals (n=30) answer control vs. key questions in the ADMIT test. The assumption of the CIT for ADMIT was that a difference can be detected via electrodermal responses. This assumption was cross-validated, and then the test was also analyzed to see whether mouse movements can also be predictive of deception.

Electrodermal Response:

The polygraph is based on the assumption that a guilty person will experience a heightened electrodermal response (caused by arousal and stress) when answering key questions deceptively compared to answering control questions truthfully (Krapohl et al. 2009). Results of ADMIT experiment confirmed that this effect was present in this experiment. A linear mixed model predicting deception (control vs. key item) was specified based on electrodermal responses nested within each participant. In other words, this experiment examined deviations from individual electrodermal baselines by examining z-scores. Thus, participants were only compared to their own electrodermal baseline to detect anomalies.

It was found that the peak electrodermal response was a significant predictor of key items ($p<0.05$, $z=1.911$, $n=30$, one-tailed). In other words, after controlling for individual differences, people were significantly more likely to experience a higher electrodermal response on the key items than on the control item. Similarly, it was found that the minimum electrodermal responses were significant predictors of control items ($p<0.05$, $z=-1.743$, $n=30$, one-tailed). In other words, after controlling for individual differences, people were more likely to experience a lower electrodermal response on the control questions compared to the key questions.

Mousing Behavior:

Complementing the electrodermal responses, it was also found that several significant mousing differences existed in how guilty participants answered key vs. control questions. Linear mixed models was used to predict deception (key vs. control item) based on mousing behavior nested within each participant. In other words, models were constructed at each time interval to find deviations from individual mousing baselines through examining z-scores. Thus, participants were only compared to their own mousing baseline to detect anomalies. The results are described below.

Figure 4:
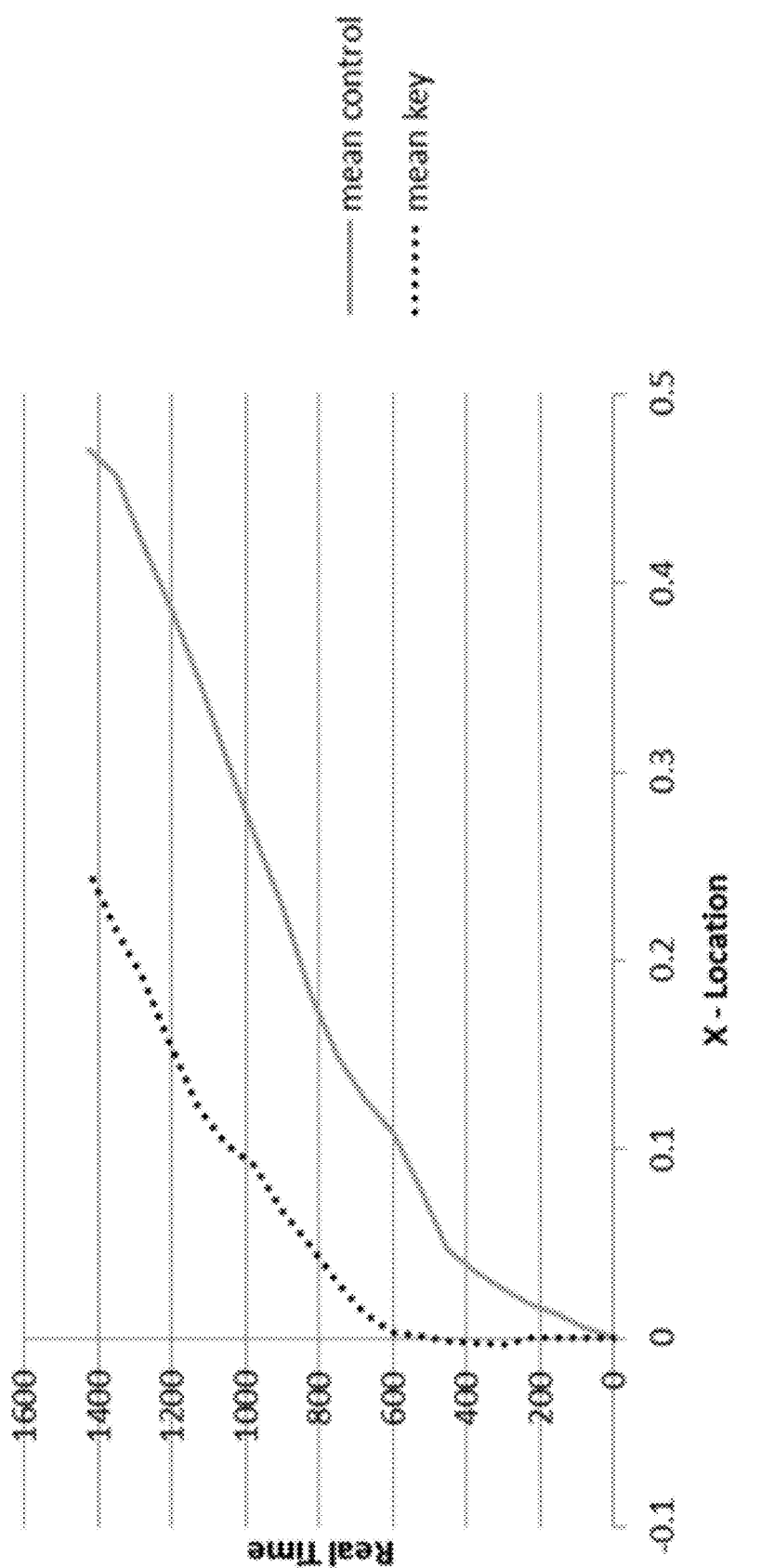
FIG. 4 is a graph of X-location by real time for guilty participants in a simulated ADMIT test.
Figure 5:
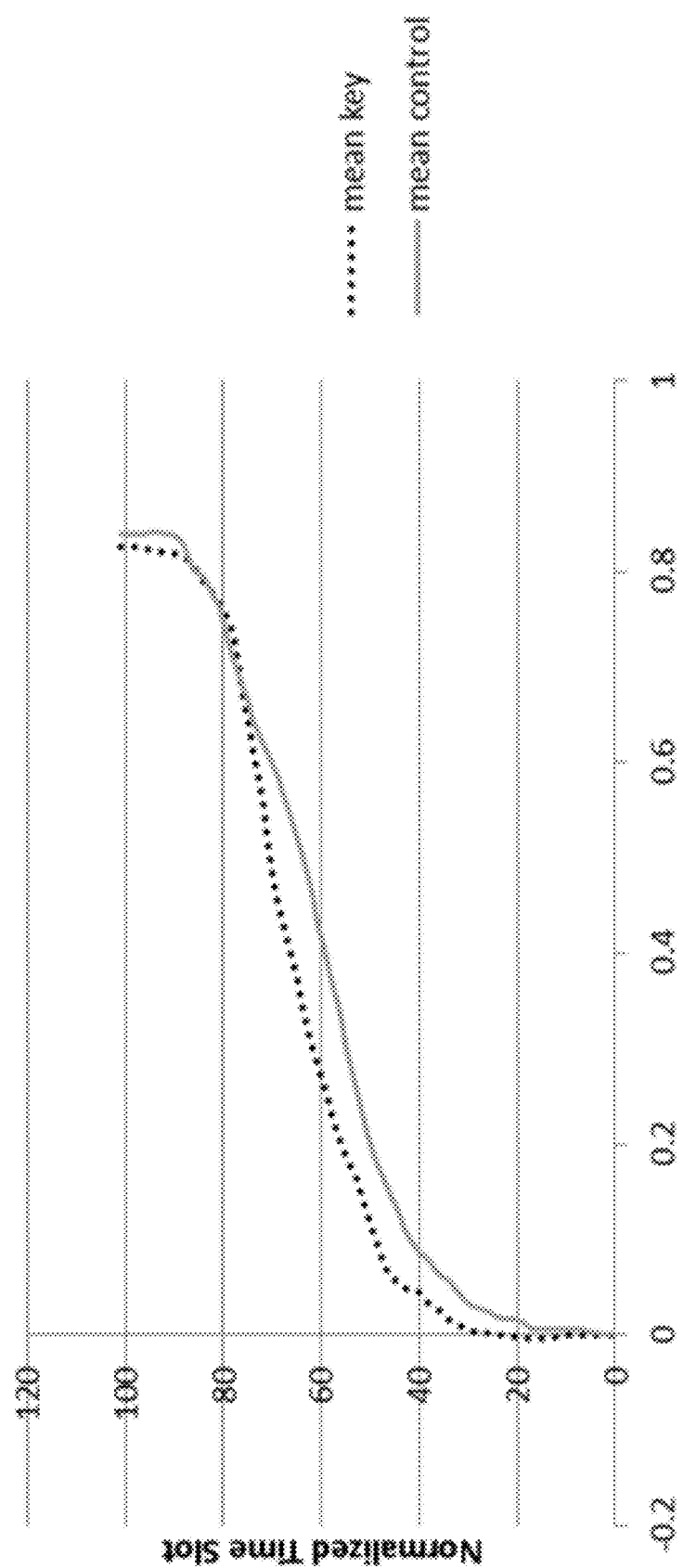
FIG. 5 is a graph of X-locations by normalized time for guilty participants in a simulated ADMIT test.

First, participants' mouse trajectories on key items (deceptive responses) showed more attraction toward the opposite answer than did their trajectories on control items (truthful responses). This was apparent in both the x-location by raw-time graph (FIG. 4) and the x-location by normalized time graph (FIG. 5). The raw-time graph for x-locations (FIG. 4) shows that participants experienced an initial delay in moving horizontally on key questions (~600 ms). After this delay, the rate at which participants moved along the x-axis when lying was slower than when telling the truth. For example, at time interval 526-600 ms, the average difference between truthful and deceptive responses in x-location was 0.0778 (on a transformed scale between 0 and 1); At time interval 1426-1500 ms, however, the difference in x-location was 0.2217; honest responses had traveled nearly twice as far on the x-axis as the deceptive responses at this time interval.

To validate these observations, a linear mixed model was specified at each time interval (~75 ms) to identify anomalies—a total of 20 independent tests were conducted. The results showed that the individuals' trajectories for key and control questions were significantly different on the x-axis at a $p<0.1$ level ($z>1.282$, $n=30$) for all time slots between 301 ms-1500 ms (16 sequential time slots). Furthermore, the trajectories were significantly different at a $p<0.05$ level ($z>1.645$, $n=30$) for a subset of these times slots between 901 ms-1500 ms (8 sequential time slots).

Running multiple independent tests as done in this study may cause alpha slippage—i.e., something being significant due to random chance. To determine the extent alpha-slippage might account for the results, the probability were computed of having multiple significant tests in a row. The probability of having 16 time slots significant in a row at a $p<0.1$ level due to random chance is $0.1 \times 10^{16}$ ($p<0.0000000000000001$). The probability of having 8 time slots significant in a row at a $p<0.05$ level due to random chance is $0.05 \times 10^8$ ($p<0.0000000000390625$). Hence, it can be concluded that for the 20 independent tests run, the significant difference in the trajectories was likely not due to alpha-slippage.

Next, by examining x-location by normalized time, the present inventors were able to measure spatial attraction toward an opposite choice. Similarly to the present inventors previous analysis, a linear mixed model predicting deception (control vs. key item) based on x-location was specified for each standardized time slot (101 independent tests conducted). Complementing the present inventors' previous findings, it was found that the normalized trajectories were significantly different at a $p<0.1$ level ($z>1.282$, $n=30$) from time slots 45-48 (4 sequential time slots), 55-69 (15 sequential time slots), and again in time slots 92-94 (3 sequential time slots).

Figure 6:
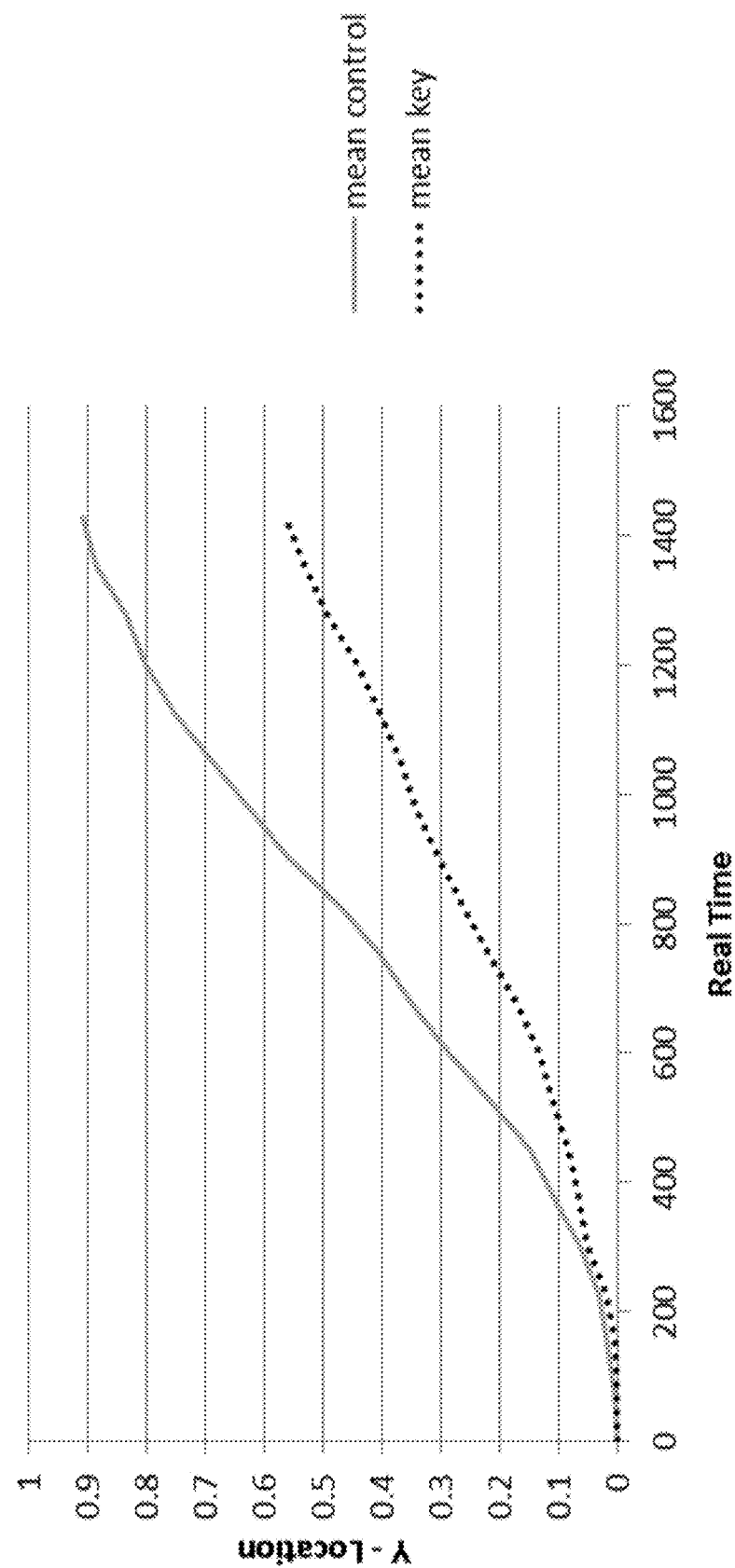
FIG. 6 is a graph of Y-locations by real time for guilty participants in a simulated ADMIT test.
Figure 7:
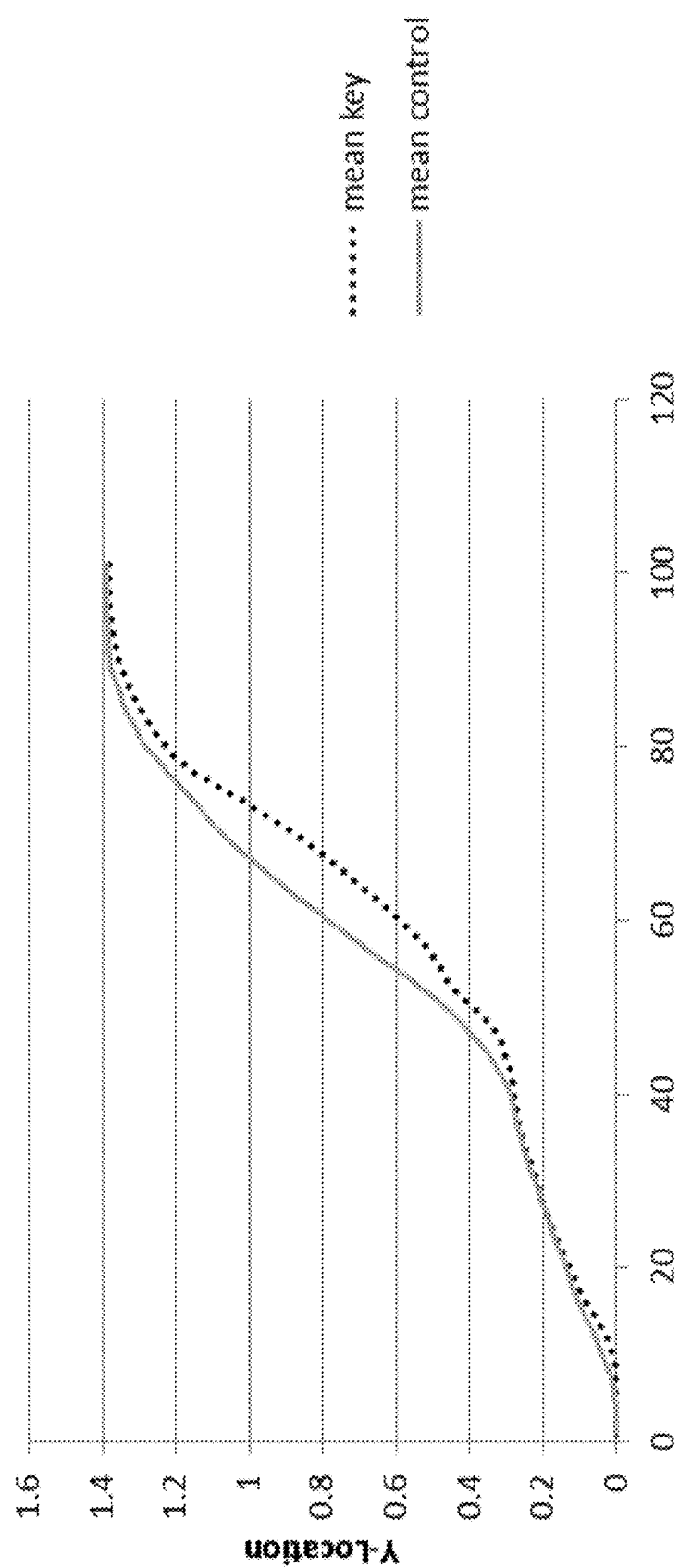
FIG. 7 is a graph of Y-locations by normalized time for guilty participants in a simulated ADMIT test.

On the y-axis, the mouse trajectories during key questions (deceptive responses) showed increased hesitancy in moving upward. This was apparent in both the y-location by raw-time graph (FIG. 6) and the y-location by normalized time graph (FIG. 7). The raw-time graph for y-locations (FIG. 6) revealed that participants started moving upward at approximately the same time when deceiving as they did when telling the truth. However, the rate of upward movement was slower. For example, the difference at the 451-525 ms time slot was 0.0675; whereas the difference at the 1426-1500 ms time slot was 0.3472.

Specifying a linear mixed model for each time period (20 independent tests were conducted), whether individuals' trajectories while being deceptive was significantly different from their trajectories while being truthful was tested. It was found that the key item (deceptive) trajectories were significantly different at a p<0.1 level (z>1.282, n=30) from 451 ms to 1500 ms (15 sequential time slots); and within this time period, the trajectories were different at a p<0.5 level (z>1.645, n=30) from 826 ms to 1500 ms (9 sequential time slots).

Using the y-location by normalized time, vertical hesitancy toward answering a key question deceptively was measured. Specifying a linear mixed model for each time slot (101 independent test runs), whether the deceptive and truthful trajectories were significantly different was tested. It was found that the key item trajectories were significantly different at a p<0.1 level (z>1.282, n=30) from time slot 56-74 (19 sequential time slots) and significantly different at a p<0.05 level (z>1.645, n=30) from timeslot 64-70 (7 sequential time slots). The trajectories were again different at a p<0.1 level (z>1.282, n=30) on the y-axis near the end of the movement from time slot 88-92 (5 sequential time slots) and, within this, at a p<0.5 level (z>1.645, n=30) from 89-90 (2 sequential time slots).

Figure 8:
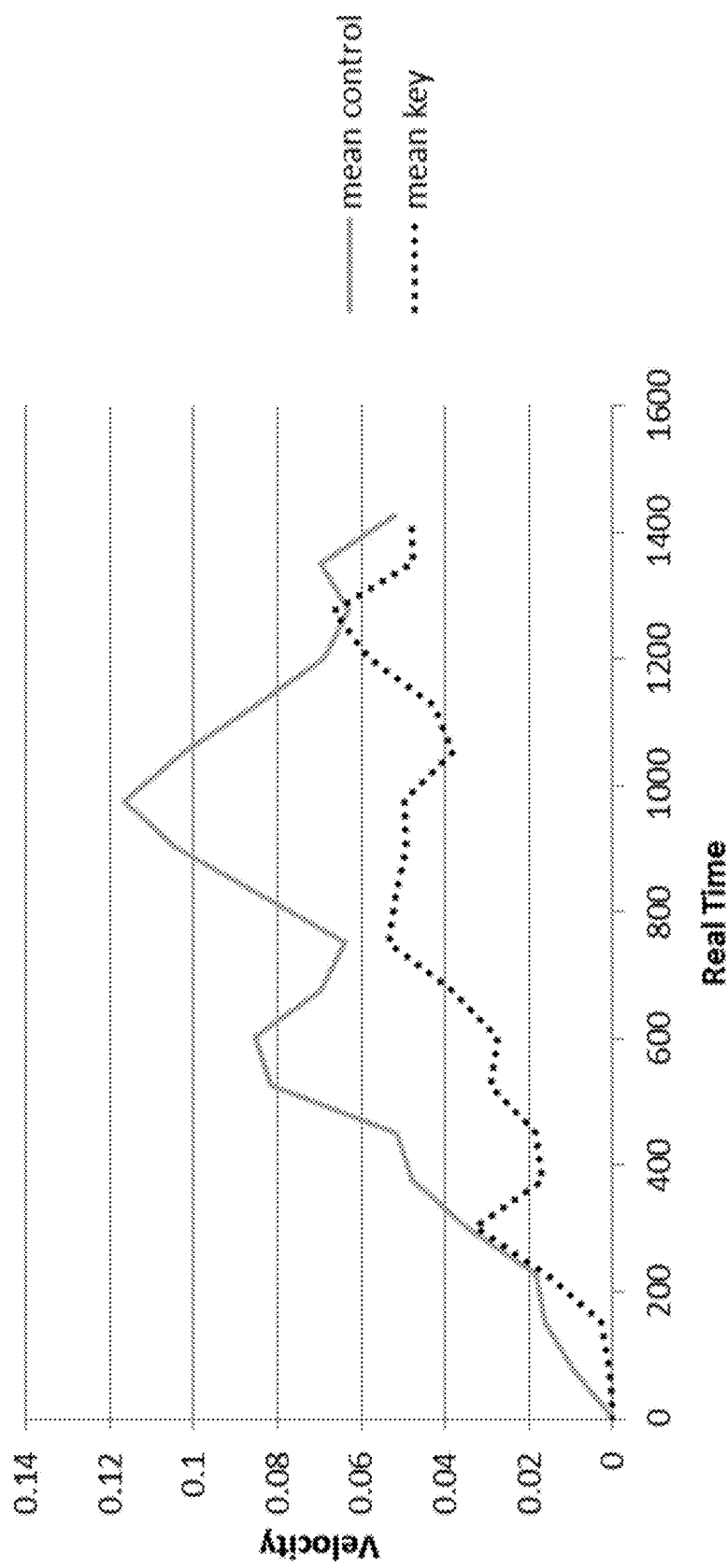
FIG. 8 is a graph of velocity by real time for guilty participants.
Figure 9:
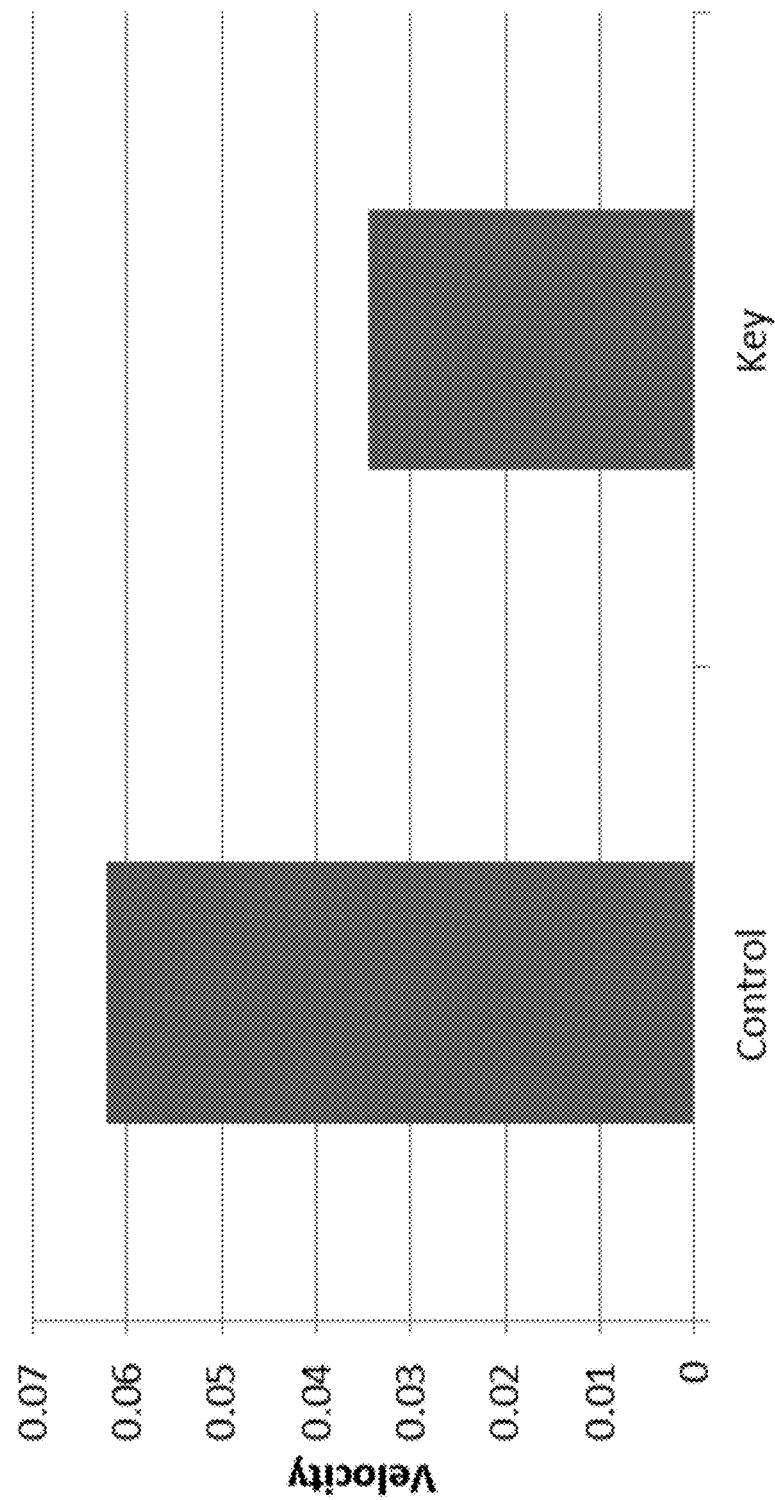
FIG. 9 is a bar graph showing mean velocity for guilty participants on control vs. key questions.

As the rates of movement along the x-axis and y-axis were slower for deceptive responses than for truthful responses, not surprisingly deceptive responses also had a slower overall velocity. See FIG. 8. Specifying a linear mixed model for each time slot (20 independent tests), it was found that deceptive responses showed a significantly lower velocity at the peaks in FIG. 8 from 376 ms-675 ms (4 sequential time slots) and from 901 ms to 1200 ms (4 sequential time slots) at a p<0.1 level (z>1.282, n=30). When examining the mean velocity across the entire movement, guilty participants showed significantly lower velocity on key question (p>0.01, z=-2.494, n=30). See FIG. 9. Velocity on key questions was nearly half.

Figure 10:
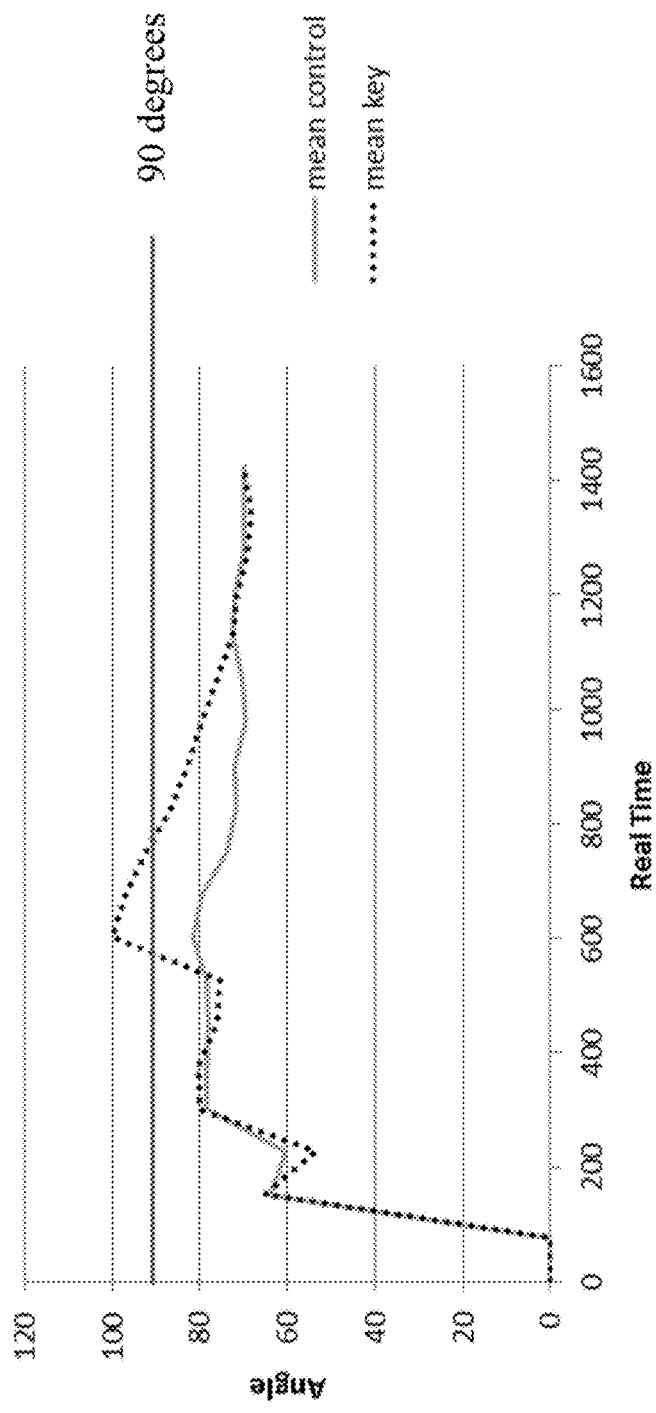
FIG. 10 is a graph showing angles by real time for guilty participants.

Also in support that trajectories show attraction toward the truthful answer while moving toward the deceptive answer, data analysis showed that when guilty participants were deceptive, they actually had movement toward the truthful answer for a short period of time before moving toward the deceptive answer as shown in FIG. 10. In this figure, any value over 90 degrees indicates movement along the x-axis in the opposite direction (going left toward the truthful response). As seen in the chart, deceptive responses on average move toward the truthful answer for a few hundred milliseconds before totally committing to the deceptive answer. Specifying a linear mixed model for each time period (20 independent tests), it was found that this difference is significant from 601 ms to 1050 ms at a p<0.1 level (z>1.282, n=30) (6 sequential time slots) and, within this time frame, significant from 601 ms to 900 ms at a p<0.05 level (z>1.645, n=30) (4 sequential time slots).

Guilty and Innocent Key Item Trajectories:

In this experiment, whether differences in mouse movement can be detected between how guilty and innocent people answer key items were tested. The first test was whether an electrodermal response was present, next test was whether differences in mousing behavior existed.

Electrodermal Response:

Typically, comparisons only within subject are made in a polygraph examination because of individual differences. Hence, a comparison of electrodermal activity in how guilty and innocent people answer key questions is not normally conducted. This was cross validated in the experiment by the present inventors and found no differences in electrodermal responses between how innocent and guilty people answered key questions.

Figure 11:
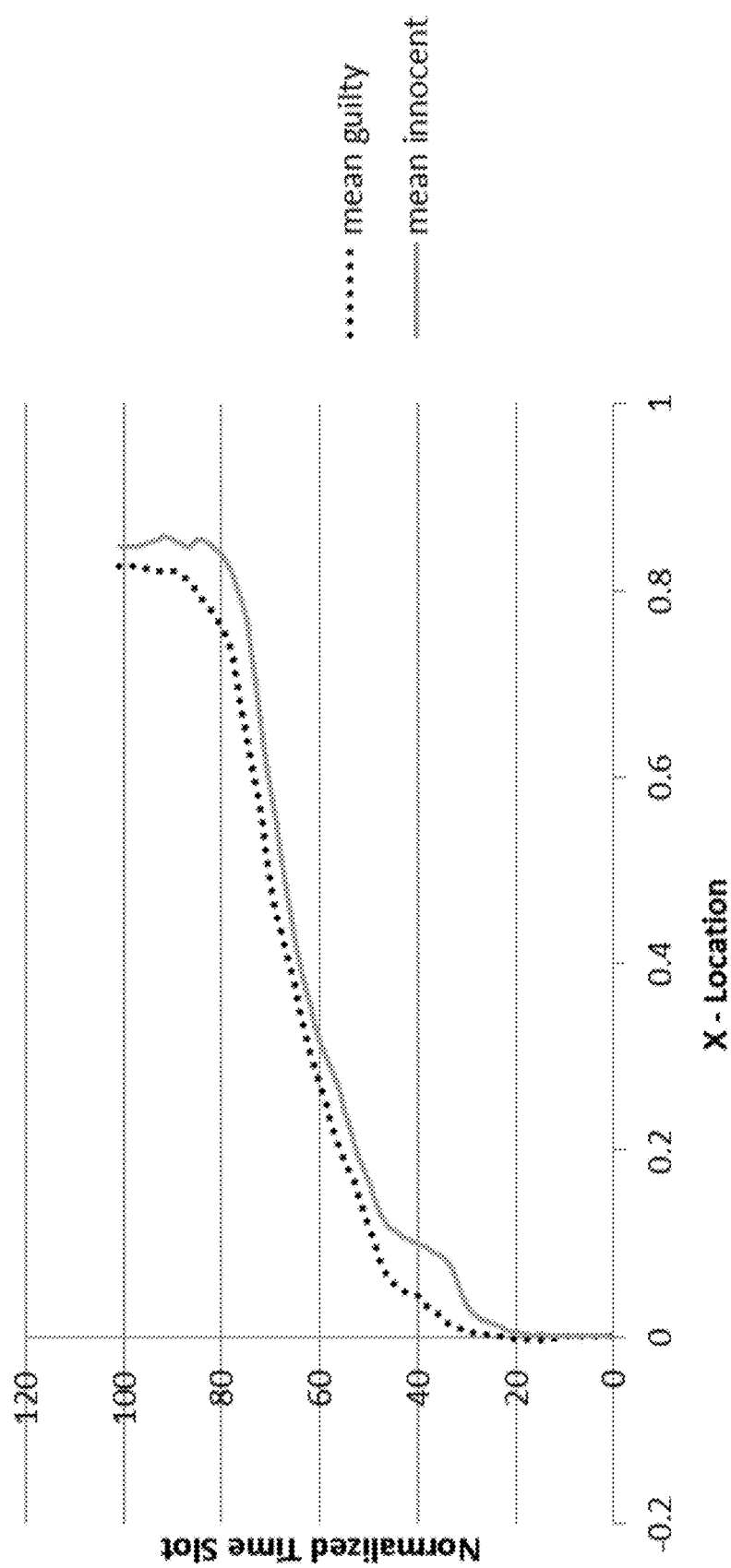
FIG. 11 is a graph of X-locations by normalized time for key items.

Mousing Behavior:

Although electrodermal responses did not reveal differences, it was found that mousing behavior did show a significant difference. Guilty individuals showed a more tentative commitment toward the opposite answer (for the guilty individual, the truthful answer) than did the innocent individuals on key items. FIG. 11 is a graph of the x-location by normalized time slots for guilty and innocent participants while answering the key questions. As can be seen, guilty individuals' mouse trajectories were more biased toward the opposite (i.e., the truthful) choice than those of innocent individuals. Using a series of t-tests (e.g., Duran et al. 2010) for each normalized time slot (total of 101 independent t-tests), it was found that the innocent and guilty participant trajectories are significantly different at a p<0.1 level (t>1.295, df=65) from time slots 1-9 (9 sequential time slots), 25-39 (15 sequential time slots), 72-101 (30 sequential time slots). Within these intervals, the trajectories were significantly different at a p<0.05 level (t>1.669, df=65) from time spots 1-2 (2 sequential time slots), 5-6 (2 sequential time slots), 28-36 (9 sequential time slots), and 73-101 (29 sequential time slots).

Figure 12:
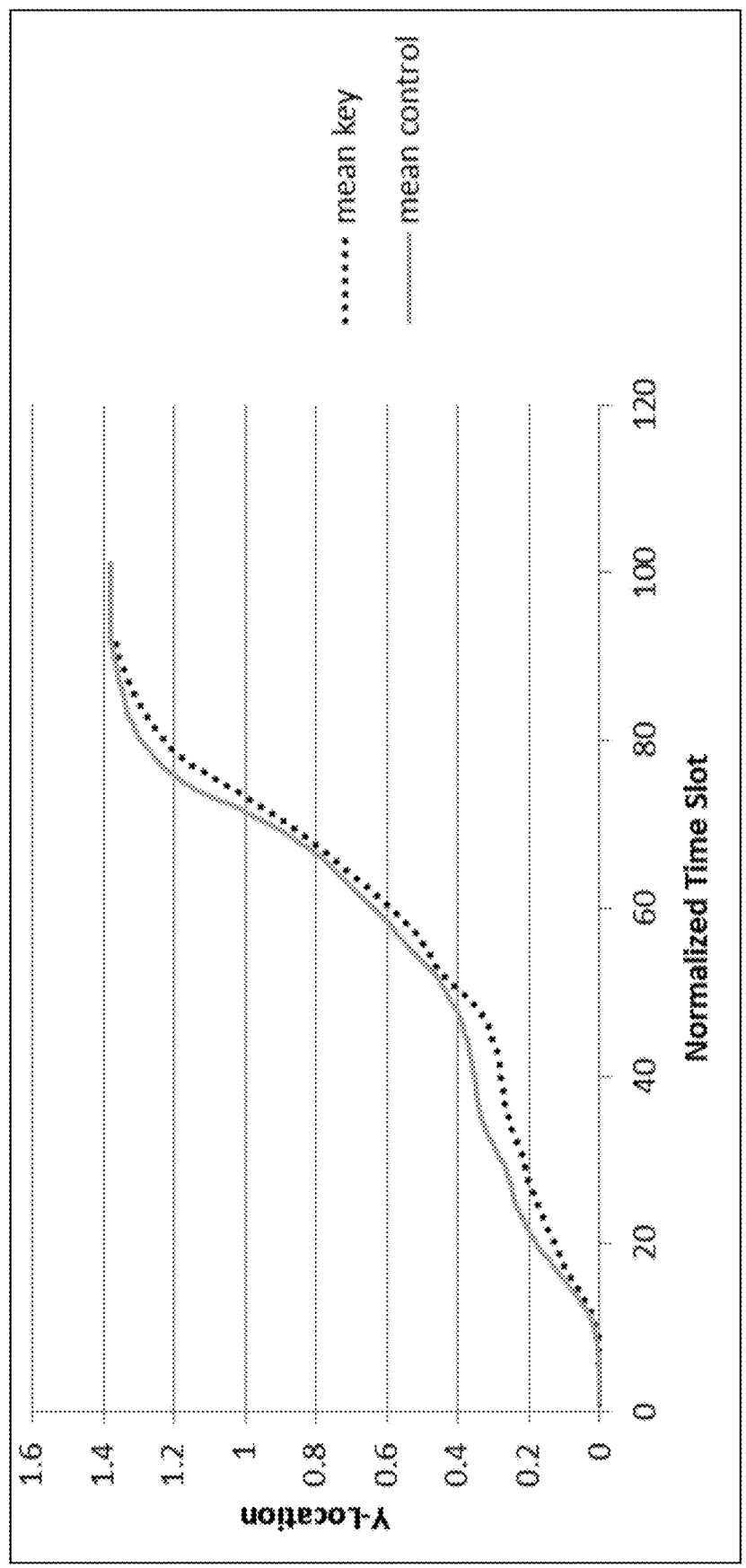
FIG. 12 is a graph of Y-locations by normalized time for key items.

FIG. 12 is a graph of the y-location by normalized time slots for guilty and innocent participants while answering the key questions. As can be seen, guilty individuals' mouse trajectories also were more hesitant toward moving upward toward the deceptive answer than were innocent participants moving upward toward the truthful answer. Using a series of t-tests (e.g., Duran et al. 2010) for each normalized time slot (total of 101 independent t-tests), we found that the innocent and guilty participant trajectories are significantly different at a p<0.1 level (t>1.295, df=65) from time slots 74-92 (19 sequential time slots). Within these intervals, the trajectories were significantly different at a p<0.05 level (t>1.669, df=65) from time spots 80-85 (6 sequential time slots).

In the normal administration of the polygraph, an analysis between how guilty and innocent people answer key items is not normally done; as expected electrodermal was not able to differentiate responses between the guilty and innocent. However, mouse movements was able to significantly differentiate between the guilty and innocent.

Guilty and Innocent Control Item:

Whether differences exist in how guilty and innocent people answer control items was also tested. In this case, the difference is believed to be due solely to the arousal associated with committing the mock theft, and not due to being deceptive on a question.

Electrodermal Response:

The polygraph assumes that no-significant electrodermal difference will be found between innocent and guilty participants when answering control questions. Supporting this assumption, our analysis of electrodermal responses revealed no significant differences between innocent and guilty participants when responding to control items.

Figure 13:
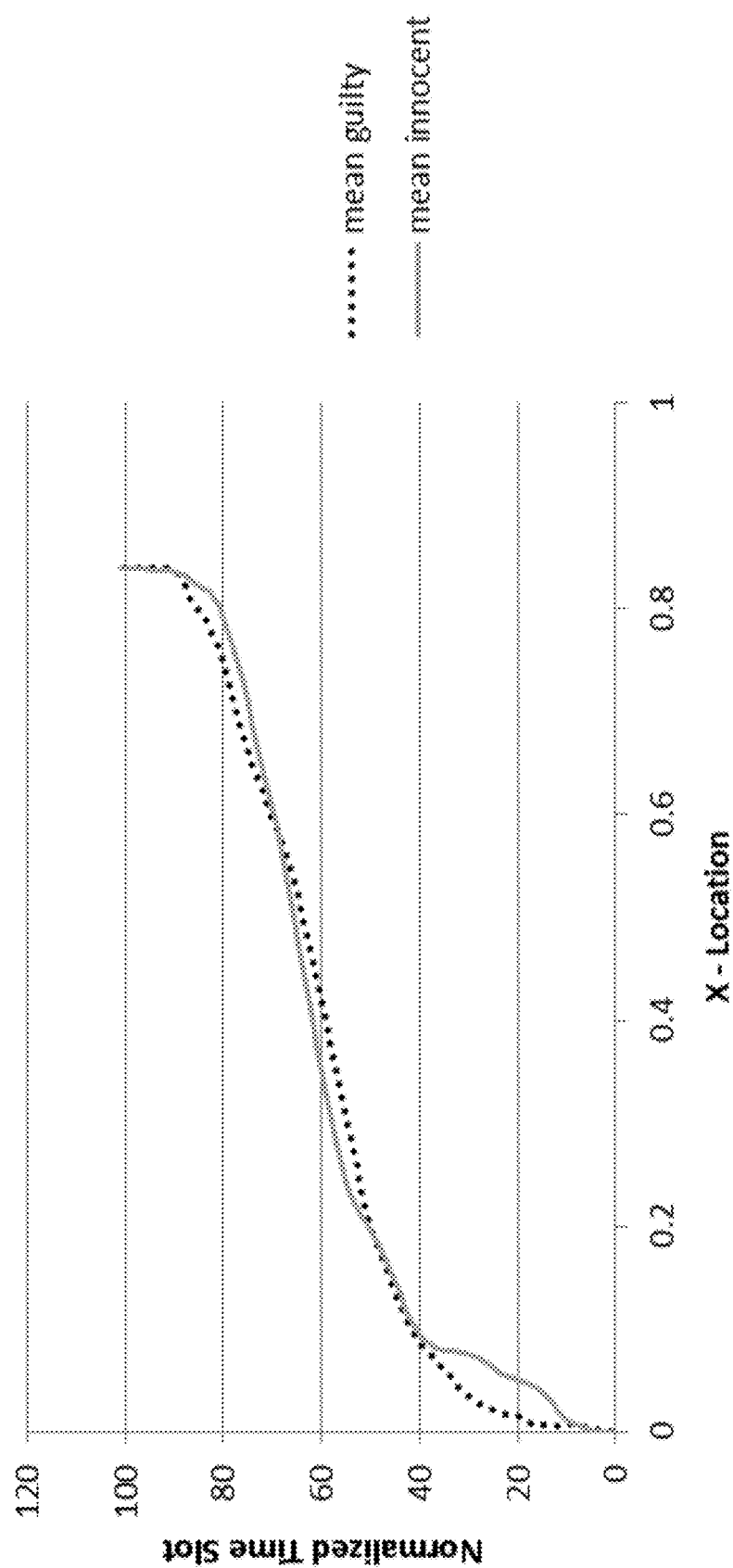
FIG. 13 is a graph of X-location by normalized time for control items.
Figure 14:
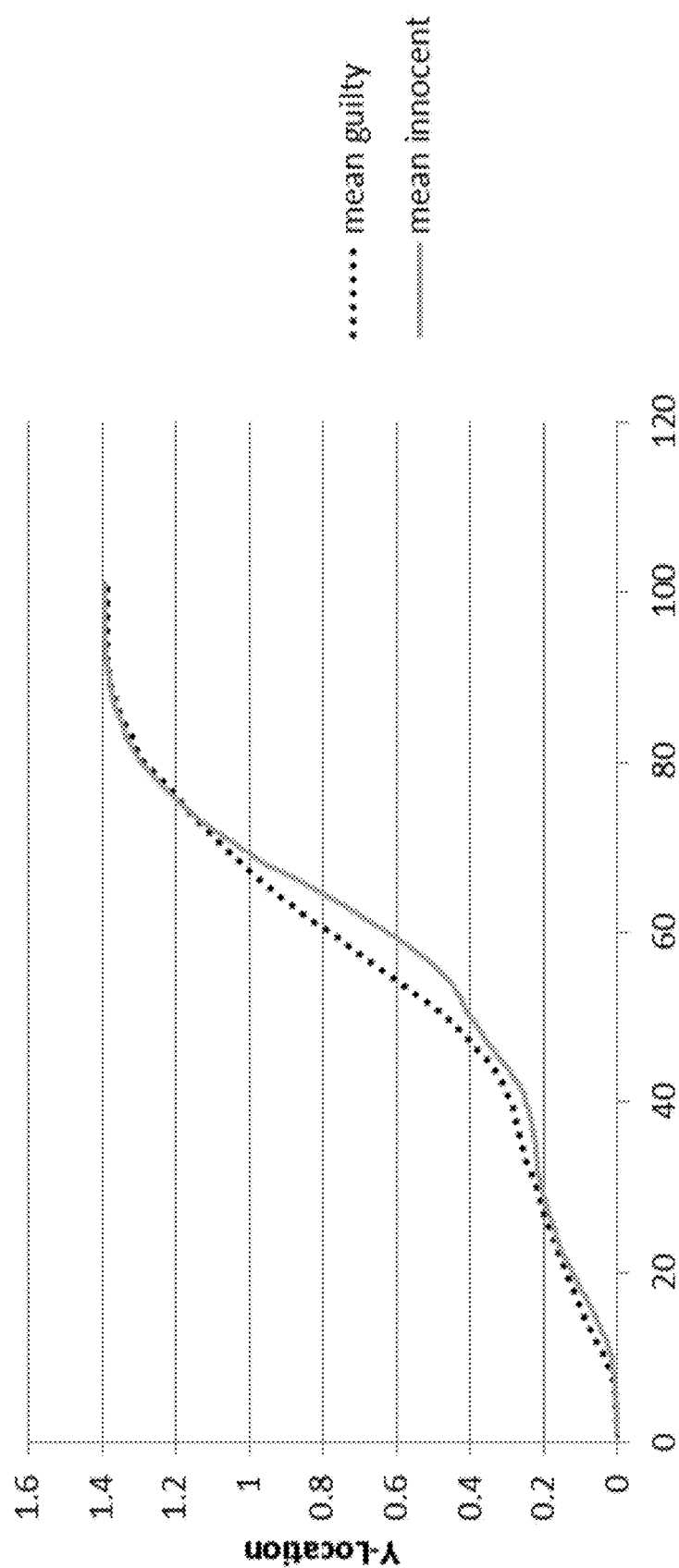
FIG. 14 is a graph of Y-location by normalized time for control items.

Mousing Behavior:

Although no differences were found in electrodermal data, differences in mouse behavior were found that may be suggestive of a task-induced search bias by guilty participants (a fundamentally different cognitive response compared to being deceptive). FIG. 13 and FIG. 14 show the x,y-locations, respectively, by normalized time slots for guilty and innocent responses to control questions. As a reminder, each participant answered 4 control questions regardless whether they were guilty or innocent. To test for significant differences in trajectories, a linear mixed model was conducted nesting participants' responses within each control item (e.g., finding anomalies from the baseline within each of the 4 control items through examining z-scores).

The significant difference in x-locations took place at the beginning of the mouse trajectory. FIG. 13. Trajectories between guilty and innocent individuals were different at a $p<0.1$ level ($z>1.282$, $n=66$) between time slots 12-31 (20 sequential time slots) and, with in this, different at a $p<0.05$ level ($z>1.645$, $n=66$) between slots 15-28 (14 sequential time slots) at a $p<0.05$ level ($z>1.645$, $n=66$). Whereas the innocent person started moving horizontally almost immediately to answer the question, the guilty person had a small hesitancy before committing to the answer. However, this difference only lasted a short while, after which the guilty person had moved as far or further horizontally along the x-axis than the innocent person.

Interestingly, when examining the y-location on a time normalized scale, both guilty and innocent participants moved upward at about the same rate prior to the 'decision period' shown on the x-location chart (a little before time slot 40). However, immediately following this 'decision period', guilty participants' progressed along the y-axis at a faster rate than innocent participants. Thus, during the middle interval, guilty participants are significantly further along the y-axis than innocent participants. This difference is significant at a $p<0.1$ level ($z>1.282$, $n=66$) from time slots 52-66 (15 sequential time slots) and at a $p<0.05$ level ($z>1.645$, $n=66$) from time slots 53-64 (12 sequential time slots).

This mousing behavior is suggestive of a task-induced search bias: Anticipating a question that will incriminate them, guilty insiders take a fraction of a second longer to determine how to respond (shown on the x-axis) rather than habitually responding as innocent respondents do. Realizing that the question is irrelevant to the crime, they make a quick and efficient move toward the correct answer catching up to innocent participants on the x-axis and passing them on the y-axis.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A real-time behavioral biometric-based deception analysis system for determining whether a subject is truthful or deceptive to a question of interest that is presented on a display screen, said system comprising:
   a data interception unit configured to intercept input in real-time from a subject that is directed to a question presented on a display screen, wherein the data interception unit is configured to passively collect a pointing device usage characteristic in real-time;
   a behavior analysis unit operatively coupled to said data interception unit to receive the passively collected pointing device usage characteristic; and
   a behavior comparison unit operatively coupled to said behavior analysis unit, wherein said system dynamically monitors and passively collects behavioral biometric information in real-time, and translates said behavioral biometric information into representative data comprised of cursor trajectory data, wherein the representative data is normalized against population data and the cursor trajectory data is rescaled to account for screen resolution, stores and compares results, and outputs a result associated with truthfulness or deception of the subject to the question of interest presented on the display screen.

2. The behavioral biometric-based deception analysis system of claim 1, wherein said behavior comparison unit is operatively connected to an application for presenting a question on the display screen such that said behavior comparison unit influences the next question presented on the display screen using a decision tree structure based on the result.

3. The behavioral biometric-based deception analysis system of claim 1, wherein said pointing device usage characteristic comprises movement of said pointing device between the starting position of said pointing device and the answer selected by the subject on the display screen, the elapsed time between presentation of the question on the display screen and the selection of the answer by the subject, or a combination thereof.

4. The behavioral biometric-based deception analysis system of claim 3, wherein said pointing device usage characteristic comprises speed, total distance travelled, initial direction of movement, total response time, change in direction on the x-axis, change in direction on the y-axis, acceleration, idle time, area under the curve, amount of deviation, reaction time, changes in angle, or a combination of two or more thereof.

5. The behavioral biometric-based deception analysis system of claim 1, wherein the behavior comparison unit compares the result of the subject's behavioral biometric to a reference behavioral biometric.

6. The behavioral biometric-based deception analysis system of claim 5, wherein said reference behavioral biometric comprises the subject's behavioral biometric to a non-sensitive question.

7. The behavioral biometric-based deception analysis system of claim 5, wherein said reference behavioral biometric comprises an average behavioral biometric to the same question presented on the display screen of a plurality of subjects.

8. The behavioral biometric-based deception analysis system of claim 1, wherein said system is suitably configured for real-time deception analysis.

9. The behavioral biometric-based deception analysis system of claim 1, wherein said data interception unit is further configured to passively collect keyboard usage characteristic of the subject.

10. A method for determining whether a subject is truthful or deceptive to a question of interest in real-time, said method comprising:
   (a) presenting a first key question and a plurality of answers on a display screen;
   (b) allowing a subject to select an answer using a pointing device;

(c) passively collecting the subject's pointing device usage characteristic in real-time, wherein the pointing device usage characteristic is normalized against population data and rescaled to account for screen resolution;

(d) comparing subject's pointing device characteristic with a reference pointing device usage characteristic to determine whether the subject is truthful or deceptive to the question of interest; and (e) displaying a result associated with truthfulness or deception of the subject to the question of interest.

11. The method of claim 10 further comprising the steps of:

(a) presenting a first control question and a plurality of answers on a display screen;

(b) allowing the subject to select an answer using the pointing device;

(c) passively collecting pointing device usage characteristic of the subject in real-time; and (d) storing passively collected pointing device usage characteristic of the subject as the reference pointing device usage characteristic.

12. The method of claim 10, wherein said reference pointing device usage characteristic is an average pointing device usage characteristic of a plurality of subjects for the same question of interest.

13. The method of claim 10, wherein said pointing device usage characteristic comprises pointing device movement between the starting position of pointing device and the answer selected by the subject on the display screen.

14. The method of claim 13, wherein said pointing device usage characteristic comprises at least one of speed, total distance travelled, initial direction of movement, total response time, change in direction on the x-axis, change in direction on the y-axis, idle time, area under the curve, amount of deviation, reaction time, applied pressure, changes in angle, the pattern of a users' acceleration or deceleration during a movement, the precision of movements, the click latency, or click pressure.

15. The method of claim 10, further comprising repeating all of steps (a)-(d) with a second key question prior to step (e).

16. The method of claim 15, wherein the reference pointing device usage characteristic for the second key question is an average pointing device usage characteristic of a plurality of subjects for the same question of interest.

17. The method of claim 15, wherein the pointing device usage characteristic for the second key question comprises pointing device movement between the starting position of pointing device and the answer selected by the subject on the display screen.

18. The method of claim 17, wherein the pointing device usage characteristic for the second key question comprises at least one of speed, total distance travelled, initial direction of movement, total response time, change in direction on the x-axis, change in direction on the y-axis, idle time, area under the curve, amount of deviation, reaction time, applied pressure, changes in angle, the pattern of a users' acceleration or deceleration during a movement, the precision of movements, the click latency, or click pressure.

* * * * *